US007704736B2

(12) United States Patent
Scholer et al.

(10) Patent No.: US 7,704,736 B2
(45) Date of Patent: Apr. 27, 2010

(54) COMPOSITIONS FOR THE DERIVATION OF GERM CELLS FROM STEM CELLS AND METHODS OF USE THEREOF

(75) Inventors: Hans R. Scholer, Muenster (DE); Karin M. Huebner, Kennett Square, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/494,795

(22) PCT Filed: Nov. 12, 2002

(86) PCT No.: PCT/US02/36260

§ 371 (c)(1),
(2), (4) Date: Jul. 26, 2004

(87) PCT Pub. No.: WO03/046129

PCT Pub. Date: Jun. 5, 2003

(65) Prior Publication Data

US 2005/0015824 A1 Jan. 20, 2005

Related U.S. Application Data

(60) Provisional application No. 60/338,329, filed on Nov. 9, 2001.

(51) Int. Cl.
*C12N 5/00* (2006.01)
*C12N 5/02* (2006.01)
*C12N 5/06* (2006.01)
*C12N 5/10* (2006.01)

(52) U.S. Cl. ..................... 435/377; 435/354
(58) Field of Classification Search ............. 435/325, 435/377
See application file for complete search history.

(56) References Cited

U.S. PATENT DOCUMENTS 6,781,030 B1 * 8/2004 Baguisi et al. ............. 800/24
2005/0148070 A1 7/2005 Thomson

OTHER PUBLICATIONS

Wilmut et al. (1997, Nature, 385: 810-813).*
Lira et al., 1990, PNAS, USA, 87: 7215-7219.*
Nakagawa et al. 2000, Arch. Histol., Cytol., 63: 229-241.*
Toyooka, et al., 2003, PNAS, USA, 100: 11457-11462.*
Thomson, et al., 1995, PNAS, USA, 92: 7844-7848.*
Kato et al. 1999, Molecular Reproduction and Development, 54: 43-48.*
Pera et al. 2000, Journal of Cell Science, 113: 5-10.*
Clark, et al., 2004, Human Molecular Genetics, 13: 727-739.*
Clark et al., 2004, Stem Cells, 22: 169-179.*
Thomson et al., 1998, Science, 282: 1145-1147.*
Ostenfeld et al., 2002, Developmental Brain Research, 134: 43-55.*
Eppig and O'Brien, 1996, Biology of Reproduction, 54: 197-207.*
Yoshimizu et al., 1999, Develop. Growth Differ. 41: 675-684.*
Nordhoff et al., 2001, Mammalian Genome 12: 309-317.*
Guan, K., et al., "Embryonic Stem Cells in vitro—Prospects for Cell and Developmental Biology . . . ," ALTEX, 16:135-141, (1999).
Pedersen, R.A., "Studies of in vitro Differentiation with Embryonic Stem Cells," Reprod. Fertil. Dev., 6:543-52, (1994).
Eppig, J.J., et al., "Mammalian oocyte growth and development in vitro," Mol Reprod Dev, 44(2): p. 260-73, (1996).
Zenzes, M.T., et al., "Studies on the function of H-Y antigen: dissociation and reorganization . . . ," Cytogenet Cell Genet, 20(1-6): p. 365-72 (1978).
Maltsev, V.A., et al., Embryonic stem cells differentiate in vitro into cardiomyocytes representing sinusnodal . . . , Mech Dev, 44(1): p. 41 (1993).
McLaren, A., "Mammalian germ cells: birth, sex, and immortality," Cell Struct Funct, 26(3): p. 119-22. (2001).
O'Shea, K.S., "Embryonic stem cell models of development," Anat Rec, 257 (1): p. 32-41, (1999).
Bremer, S. et al., "Pluripotent stem cells of the mouse as a potential in vitro model for . . . ," Mutat Res, 444(1): p. 97-102, (1999).
Brustle, O., et al., "Embryonic stem cell-derived glial precursors: a source of myelinating transplants," Science, 285(5428): p. 754-6, (1999).
De Felici, M., S. Dolci, and G. Siracusa, "Involvement of thiol-disulfide groups in the sensitivity of . . . ," J Exp Zool, 1987. 243(22): p. 283-87, (1987).
Dinsmore, J., et al., "Embryonic stem cells differentiated in vitro as a novel source of cells for transplantation," Cell Transplant, 5(2): p. 131-43, (1996).
Donovan P.J., "The germ cell—the mother of all stem cells," Int J Dev Biol, 42 (7): p. 1043-50, (1998).
Odorico, J.S., D.S. Kaufman, and J.A. Thomson, Multilineage differentiation from human embryonic stem cell lines. Stem Cells, 19(3): p. 193-204, (2001).
Ohno, S., Y. Nagai, and S. Ciccarese, "Testicular cells lysostripped of H-Y antigen organize ovarian follicle-like aggregates," Cytogenet Cell Genet, 20(1-6): 351-64, (1978).
Ohtaka, T., Y. Matsui, and M. Obinata, "Hematopoietic development of primordial . . . ," Biochem Biophys Res Commun, 260(2): p. 475-82 (1999).
Wei, G. and A.P. Mahowald, "The germline: familiar and newly uncovered properties," Annu Rev Genet, 28: p. 309-24, (1994).
Pelton, T.A., et al., "Developmental complexity of early mammalian pluripotent cell populations in vivo and in vitro," Reprod Fertil Dev, 10(7-8): p. 535-49, (1998).
Rathjen, J. et al., "Mouse ES cells: experimental exploitation of pluripotent differentiation potential," Curr Opin Genet Dev, 11(5): p. 587-94, (2001).

(Continued)

*Primary Examiner*—Joanne Hama
(74) *Attorney, Agent, or Firm*—Dann, Dorfman, Herrell & Skillman; Robert C. Netter; Kathleen D. Rigaut

(57) ABSTRACT

Compositions and methods are provided for the reproducible derivation of germ cells and oocytes and spermatogonia therefrom. Also provide are methods of use of the same in reproductive and therapeutic cloning protocols.

19 Claims, 5 Drawing Sheets

OTHER PUBLICATIONS

Figure 2A:
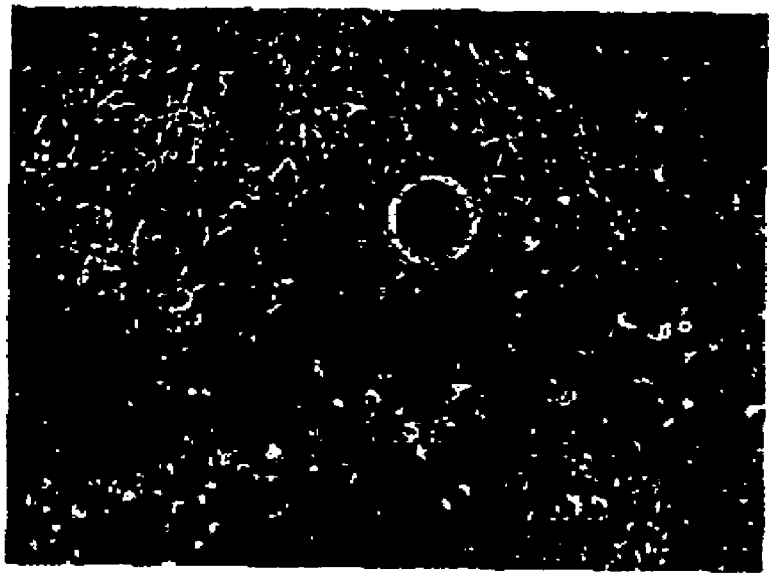

Rathjen, P.D., et al., "Properties and uses of embryonic stem cells: prospects for application to human biology and gene therapy," Reprod Fertil Dev, 10(1): p. 31-47 (1998).

Resnick, J.L., et al., "Long-term proliferation of mouse primordial germ cells in culture," Nature, 359(6395): p. 550-1, (1992).

Rich, I.N., "Primordial germ cells are capable of producing cells of the hematopoietic system in vitro," Blood, 86(2): p. 463-72, (1995).

Rodda, S.J., et al., "Embryonic stem cell differentiation and the analysis of mammalian development," Int J Dev Biol, 46(4): p. 449-58, (2002).

Sato, M. and T. Nakano, "Embryonic stem cell," Intern Med, 40(3): p. 195-200, (2001).

Shamblott, MJ, et al., "Human embryonic germ cell derivatives express a broad range of developmentally . . . ," Proc Natl Acad Sci., 98(1):113-8, Jan 2, 2001.

Snodgrass, H.R., et al., "Embryonic stem cells and in vitro hematopoiesis," J Cell Biochem, 49(3): p. 225-30, (1992).

Tesarik, J., et al., "Immature germ cell conception-in vitro germ cell manipulation," Baillieres Best Pract Res Clin Endocrinol Metab, 14(3): p. 437-52, (2000).

* cited by examiner

```
15301 GTATATGCTG GCTTCAGCAA AATAAAACCA TACCTTCTAG GAATGGTTTC TGGGACCGGT GCTCTAACTG CAGGTATCCT GGCATCCATG GAGGCAAGGC 15400
15401 TTTATTCCTT GTGACTGGGC TTGTAGCTCA CTGGAAACTT GGAGGCTGCA ACATCTTTGG CAGGAAACCA TCTTTTCTGT CACTTCATTT GCAAGCATTC 15500
15501 TCCAGCCTTG AGTCAGTCTT TAGCAATGGA CCTTTCCCTG GCTCTCACAC CTTTGGAGAA AGACATTCCT CAAAGTCCAT GGTAACTTTG AATGAGTGTT 15600
15601 TTGCATGTAC ACATGCGTGA CCCTTAGGAG GTGTGCATGC CCATTCTTCT ATGCACACGC GTGCACACAC ACACACACAC ACACACACAC ACACACACAC 15700
15701 ACACACACAC ACTGCTTCAG AGATGGTCAC AAGCCATCAT GTTGTTGCTG ATTATTATGT TTGAGTGCTC TGCACCTGCA AGCCAGAAGA GGGCATCAGA 15800
15801 TCCCTTTTAG CCAAGATACA TTCTTACACT GTGCCTGACC CTGAGCCACA GAAATTGGGA CTTCTGGAAG GTACCCTTAA TTGCTGAGCC ATCTTACTGC 15900
15901 CCAAGATACA GGTACCAGAG GTCACAGCCA TCACAGAAAC CCAGGCTCTG GACTGCAAAG TCAAGATGCC ATTATGGCAT CCTGGATGCT ATAGCCAGTG 16000
16001 CAGGCCAGAG CTTTGAGTAA CTTGCCTCTG GGTAACTGGT AGCCAGAACA CTCTCTAGCA AAAAGAAGCT GGACAGGACT CCCTAAGGGA GTGAGTGTTC 16100
16101 CTGAGAAACC TAGCACAAAA GATACTTGGC TTTGATATG AGCCTTCAATC GGAGGCTAAG ACTGGGATAT AGGAACTTGG AGATTAGGGA TGTTAAGTAG 16200
16201 AGCATACGCA AGGCTAGCCT GGATTACACA GTAGACCTT GTATTAAAAA GCCTTCAATC CATCACAACT CCCATTCTGA ATGCTCTATC CCGACTACAT 16300
16301 GAGGGATTTG AGGCTAGCCT GGATTACACA GTAGACCCTT GTATTAAAAA AGAGTTGGGT GTCTCCTCCA GAGAGGATCT GGGTTTGAAC CTCAGCACCT 16400
16401 ACATAGTGGC TAGCAATTAT CCCTCCAGTT CCCAGAGAAC CCAGTGCCCT CTGCCGGTAT TGCATGCAAG TGTGATACCC AATCATGCAG ATCATGCAG 16500
16501 GCAAACAAAG CAGCCTTGAA TTGACCTGCT CTCCCTCTAG TTTGAGACAG GTTTTTATG ATTGCTTTGT GGACTCCAAA CATGGGCAAG GTTCCCACAT 16600
16601 TCAGGTGCTT GCTAGGCAGT GCTCTTCTAG TGAGACATCT TGTCTGCTGT GCCCGTGCAC CCCCTTCTCC TGCCTTCTAA GACCTCAGTC TGAGGCTGTT 16700
16701 AGTAGCTTGT CATGCATTTA TGGGTGAAAG CTAACCTGGG CTAACTCTGG AGCTTCCCGT AGCTTCCCGT ACCCGGAGCC TCTTCCTGGG CTCCCTCAGG 16800
16801 CAAAGATCTA GAATTCAAGG TGCTACAGG GACCCCACT TCTAGCTCTG CTAGCTAGAGC TTCTTGTGGG TGAGCAGGC GAAACTTGCG 16900
16901 ACGGACAGGG GGCTGGGGA GACCTCATCA TCTAGCTCTG CCAACACTTT ATGAGCTGAT TTCTTGTGGG TGAGCAGGC GAAACTTGCG 17000
17001 CTTCCCCATG CTGAGAGGGA ATAGCCAGGC CCTGTGGCCT GCCACCACCA CGGGAGAAGG GGCCTGAGT TTGCTGAGGC TGCCGATGGA 17100
17101 ATTGAGAATC AGTGTGGCCT TGGGCAGCA CTGAGTGGCC CTGAGCTGTG CCCTTGGGGG GGCAGCATAG GTTGGAAACC GCCCCAGCT 17200
17201 TCTCCCTTAG ACCGAGGGAC GGTTATGGCT GCAAAGTTCT GAGGTTAAC CCGGACTTGT TGAAACATGA AGTAGAACTC TGAGGAGGAG CTGGTTCCTG 17300
17301 CTTGACCTTG GGGGCAAAG GTCAGAAGGT CACCATCACT CAACTCCAGT CTGTGGCCTC TTGGAAGTCG GACATTATTG ACCAAGTCC CTGGTGATAA 17400
17401 TGAGACAGAC ATAAGAGAAC TGACGAGAAC AGGAACAGAC TTGTAGTCAG AATTAACATG ATCCGAATTC GTTCCCTTTA GTGAGGGTTA ATTCCGCGGC 17500
17501 CGC                                                                                                                                                                      17503
                |          |          |          |          |          |          |          |          |          |
               10         20         30         40         50         60         70         80         90        100
```

SEQUENCE LISTING

<160> NUMBER OF SEQ ID NOS: 4

<210> SEQ ID NO 1
<211> LENGTH: 16389
<212> TYPE: DNA
<213> ORGANISM: Artificial Sequence
<220> FEATURE:
<223> OTHER INFORMATION: Synthetic Sequence

<400> SEQUENCE: 1

| | | | | | |
|---|---|---|---|---|---|
| gcggccgcgt | aatacgactc | actatagggc | gaagaattcg | gatctcatta | cgggtggttg | 60 |
| tgagccacca | tgtggttgct | gggatttgaa | cttcggacct | ttggaagagc | agtcgggtgc | 120 |
| tcttacccac | tgagccatct | caccagcccc | tggattataa | attcttattt | gtacagtttt | 180 |
| tgttgttggt | tttgtttgtt | tgtttgtttc | aacacttggg | attgaatcca | gggtcattgg | 240 |
| agtgtttggc | ctgggttctg | ctgctgagcc | acactccata | tacttgcatg | gattgtgtct | 300 |
| tttattctat | gtggtggtgg | tggtggtggt | ggtggtggtg | gtggtggtgg | tggtggtggt | 360 |
| ggtagaggga | actcacccag | cccacctcct | ctggtttcac | tcctccacac | acacccttca | 420 |
| tccctgtcct | taccccctgc | cagtaagaaa | ctccacagga | tgtctctcta | ggagtctgag | 480 |
| aaaaaagcac | taagagaaca | agctgtttgt | tttttggggt | ttttttttggg | ggggtggggg | 540 |
| ggggagttag | aactcaggaa | atcagaacag | ggctaggtgt | ggtaatgaat | gacatagatc | 600 |
| tagtcactca | aaggctgtgt | acctctgaag | ttgagactag | cctggtttat | ataaaaagta | 660 |
| acctggtcta | tataaaaaat | tctaagttac | gccgggcgat | gatggcacat | gcctttgatc | 720 |
| ctagcacttg | ggaggcagag | gcaggcggat | ttcgaagttt | gaggccagcc | tggtctacaa | 780 |
| agtgagttcc | aggacagcca | gggctacaca | gagaaaccct | gccttgaaaa | caaacaaaca | 840 |
| aacaaacaaa | aaaccaaaaa | caaccaaaac | aaacaaacaa | aaaaacccca | aaaccaaaac | 900 |
| aaaacaaaac | aaaaagttct | aagctatgta | gaactcttgg | ggcactcgtg | atcaaagtct | 960 |
| aagcattgaa | aatctctaaa | tgccaggctt | ggtggcgcac | gcacttaata | ccagcacttg | 1020 |
| ggaggcagag | gcaggcagat | ttctgagttc | gaggccaacc | tggtctacaa | agtgagttcc | 1080 |
| atgacagcca | gggctacaca | gagaaaccct | gtctcgaaag | acaaaaaaaa | aaaaaaaaaa | 1140 |
| aaaaaaaaaa | aatctctaaa | caagccctat | caatcttccc | ttgggggtat | ggactgttat | 1200 |
| ctcttcatca | taagaggaaa | gcgaataggt | ggtgtgaagg | aggtctttgg | tggtgcagga | 1260 |
| gggagccact | ggctgcaggg | gacacagggt | acagcatggc | tccttagttg | gacatctgct | 1320 |
| tgacagaatg | agtgtctatc | tatctgtgga | cttgggaatc | aaccccaggt | attccaggag | 1380 |
| gtaagaagaa | ccactctctg | aaccagggtg | gtcttttgag | ccaccagaaa | aaacatccac | 1440 |
| catgtaattg | taaccaagta | accagtcata | accccctgca | acagcgccca | ggagactttt | 1500 |
| gaatctgaaa | caagcagaac | cacagagagg | gggaggaaag | gttatcctga | cccagagagg | 1560 |
| caaatcctct | ctggaacccc | gggagctagg | tcagatgcta | agggcatttg | tggggagggc | 1620 |
| tgggagagaa | gggccctagg | ctagcagcag | gtcctccttc | cctttaacct | ctggccatgt | 1680 |
| tgggtaggga | ctctccttga | caaacctgat | aaccaggagt | tcatttccga | gcacccacac | 1740 |

```
agtggaagaa gctagcccat cgcctaaagt tgccctttg ttctctttt ctctctctca      1800 cacaaatttt taaattttat tatttattta ttgacataat ttctctatgt atcccaggct      1860
gtctcagaac tcactttgta gaccaggctg gcctcaaact tagagatgct cctacctctg      1920
cctcctgagt actaggatta aggatatcca tcacaacacc taactgtaat aaaaatttca      1980
attttttttt ctctcttagc ctcagctgca atcacctctt ttagccagta tacctgcagg      2040
agctccagtc cataggcggg ctctcctaat gcctgaattt gactctcaaa gtgcattcac      2100
ttcctctcat tacagctctt ctgcagactc ttttatatca ggaatctcaa aacttgggtt      2160
gggcatggta ctcgccttta atcccaggag gtggaggcca gcctggtgta caaagtgagt      2220
tctaggtcag gcaggactgt aatgtctact ccttacatga acaggatagg gcctggcggg      2280
gagagagggg ggaagctagg tgggagtaag ggtggaaacg ggcaatcgtg tcaatggaag      2340
aagtaaatga tcaagacaat aggtctgttc acagcattag aaccacccaa atggtcattt      2400
ggcatcggag tcctctccct cctcccaatc ccccccccat ttgcttatct atttattttt      2460
attttatgta tgcaagcatt tttctttttt cttttttcttt ctgggttttt cgagacaggg      2520
tttctctgtg tagccctggc tgtcctggaa ctcactctgt agaccaggct agcttcgaac      2580
tcagaaatct gcctgcctct gcctcccaag tgctggaatc aaaggcaagg gccaccacac      2640
ctggcgcaag cattttcaa agatgtattt gtttatatat gtgagtacat tatctctctc      2700
ttcaggcaca ccaggagaga gagagagaga gagagagaga gagagagaga gagagagaga      2760
gagagagaat cagatcctgt cacagatggt tgtgagtcac caagtgggag ctgggatttg      2820
aactcaggac ctctggaaga gctgtcagtg cacttaacct gtgagccatc tctccagtcc      2880 tttcctctc tgttttttttt ttttttttt ttttttttt gacacagttt aaccatgtag      2940
cttaggctaa tcttcagttt gctgtgcctc agcttctgag tgtccacttg ggattgcagg      3000
agtttgccgc cttgctcagc ttacagcttg ggatgctctt ctcacagaca tccacgtact      3060
agtactgaaa gacaaagaca aacaccggtt tgcttgcaaa ctgctcaagt cttgtctagt      3120
ttgattaggc ttgagaggag accttgccag cttttcccaag aagactgtgt ggaggttggc      3180
ggtagaaggt ggggtacaga agacttgctt tcatctcaca aggtgcccca cccatctctc      3240
taacgcccaa ttttttcttta cagaggcaca gggacaactc cctacccccga cccatgtgga      3300 gtgagaaggg caggaggatg catgggaata gggctgtagt tttctttttca agttggaaga      3360 aaatggagag ttaggccagg gaaggtagtg acacccccct gggtgtcac acacacacac      3420 acacacacac acacacacac atacacacac agggaattct agcactggtg gtgtgagcaa      3480
gtaggtagct atatgtagta atataacaag atttattttg ctgagagtca tcacataagg      3540
ttcacactct aagccagcca ggtggtggtg gtggcacatg cctttaatcc cagcacttcg      3600
gagacagaga caggaggatt tctgagttcg aggccagcct ggtctacaaa gtgagttcca      3660
ggatagccag ggctacacag agaaaccctg tctcgagaga aaaaaaaaa aaaaggttca      3720 cactctgtaa attcctaact aatgtctcat tcctgtctcc ccacagctgc tcacctatgt      3780
gacatatttt agcagaaggt caggtccact ctcttaatct cttaagagtg tctgtgattt      3840
gagggacagg atcctagcgg ggagactctc cacctacaag gcagatcaag gtggctggtt      3900
atcttgaatg agtgatgtcg tggggttctg gttatcaggg gcagccttgg gtgtagtggt      3960
gaagccattt ctgcaagtct aaaaggcatt tggacactgc tcatcagaac tgggaaggca      4020
agaggatcag aagttcaagg gccttcttgg ctacgtagag tttagggggca gcctctgcta      4080 catgtaaatt tgtctcagaa gaaaaaagga aacgggcagt agtggcgaat gcctataatc      4140
```

```
ccagcacttg ggaagcagag ggcaggctga tttctgagct caaggccagc ctggtctaca    4200
gagtgagttc caggacagcc agggctacac agagaaaccc tgtctcagaa agaaaaaaaa    4260
aaaaagggag aaatagaact catttatttc aaagggagca ggcacattcc gcaagccttc    4320
tgttctgctg gtgacctatt cctaccttca gcttctagat cttttgttttt tcttttaatt    4380 tttattgtat tgtgtgtgtg tgtgtatctg agtgcaatat caatatcgaa cctctggaga    4440
tcaaatgctt ctttgaaatg accccaggg atcaaatcca tggtcgttag gctcagcaag    4500
tgtggttact tgctgagctg tcctcaggtt cctctcaggc ctcccctcaa gtctccccct    4560 ccaaccccc cccccctcc tgcccctgc aagtcttttt gattaggcaa gaaaaccaag    4620
acaaggaaag ggagatgcag ttagctaagg aatctatgcc agccagagaa actacctcct    4680
cccttccaga acatctggat ttgggaagag acgttgctgg tcccagggcg gctgggggtt    4740
ggggttgggg gaggggatg ctaaccagca aggaagctgt tcctggctgg ggcaggcctg    4800
actgagctca tgtcgctgaa actcctcatt tctccctatg gcttcatagg gagacccagc    4860
ctggatgcta acacgagtga tttccctgct ctagtctagt gtcctccgtg agtccattta    4920
actgatcacc cagtctgtga ggaggtggct gaactcacag taagaaagct gtgggggtca    4980
acgcctattg tttgtttgtt ttgttttaga caaggtctcc tgctgaggct ggctcaagct    5040
ggcctggagg actcttgtgt ttaaggctgg ccttaaattc tctttaaaag aaaatcatgt    5100
gtatatatgt gtgtccatgt aactgcagat gaccacagca gccaagagat ttctgttctc    5160
ctagctgtaa accacccaat atgggtgcta ggaacagaat tttaaagggg tcctctgaaa    5220
gagcaatgta cactcaaatg ctgagttctt tcccagcccc tagccttgga cctttgttct    5280
tatcacttcc aacgcccaag ggcaggcatt ataggtgtgg cattccgcat ctggcttccc    5340 aggataccctt ttcatgctgg tggaccatct ctggctgggg acgtgtgggc ttctctgctg    5400
tctttggttc tccagacaga actccgagac agatcttgac ttggttctaa aatacaggtg    5460
gtttgtggca agttaacgaa ttttagctca aatttggggt atttaagata ccatggtgac    5520
tcttttttgt ttgttttttct ttctttcttt tttttttta aaaagattta tttattattg    5580
tacgtaagta cttcagacac cagaagaggg tgacagattt tttttttttt tcgagacagg    5640
atttctctgt gaagccctgg ctgtcctgga actcactctg tagaccaggc tggcctggaa    5700
ctcagaaatc caccctgcctc tgcctcccaa gtgctgggat taaagccatg agttgggacc    5760
gcacccggcc caaagtgact cttaaagggg gcagagtggc acatattttc aatcctagca    5820
ctcaggaagc aaaggctggt ggatctctgt gagttcaagg ccagcctggt ctacagagtg    5880
agttccaagc catctaaggc tatgtaggga acccttgaat caaacccaaa agttagtctg    5940
atgattttct aagacccagg aggcaagaaa ctggatcaga tgagccaaca ggtctgctgt    6000
cccatctcca gggccaccag gctcacagct cgggaccagg ctagggcaca tctgtttcaa    6060
gctagttcta agaagacttg ggacttcaga caaagttgct gttaaggact gtattatact    6120
ctaggcacgc ttagggctaa cctggttgca aagccagtca ctaggcagtt aaaggactca    6180
gaatatgtct cttgtcctgg ccagtgagtc accaaaagag aaatcacaat ccataagaca    6240
aggttggtat tgaatacaga caggactgct gggctgcagg catacttgaa ctgtggtgga    6300
gagtgctgtc taggccttag aggctggccc tgggaggaac tgggtgtggg gaggttgtag    6360
cccgaccctg cccctccccc cagggaggtt gagagttctg ggcagacggc agatgcataa    6420
caaaggtgca tgatagctct gccctggggg cagagaagat ggttggggag gggtccctct    6480
cgtcctagcc cttccttaat ctgctattga ggaagctttg tgaacttggc ggcttccaag    6540
```

-continued

| | | |
|---|---|---|
| tcgctgcctt tatttaggtc ttccaactaa cctatggcac tgttccacaa tgaatgtata | 6600 |
| gaaattggga ggtgagcatg acagagtgga ggaaacggaa gattcatgga gagggccaga | 6660 |
| gagatggccc ctcagccacc ctgggggatg acttggaccc atgtggtaga aggaggggac | 6720 |
| ttccacacat gtgctatgtg tagctgtgtg taggtacata cacacccctta aaataaaacg | 6780 |
| caattttttt ttcaaagtct cagggtgaat ttggtgaagt cgatgaagct gaggcaggag | 6840 |
| aattatcagg agttcaaggg cagcttgttt tatagagaaa ggttccatct ctacctgatg | 6900 |
| aagactacca tcaagagaca ccccgcccc ccagggcacc tagagccact gaccctagcc | 6960 |
| aacagctcag gcgggctggg cccaggctca gaactctgtc ctggctatgt acactgtggg | 7020 |
| gtgctctggg cttttttgagg ctgtgtgatt caccctggcg cgccccaagg caggggtgag | 7080 |
| aggaccttga aggttgaaaa tgaaggcctc ctggggtccc gtcctaaggg ttgtcctgtc | 7140 |
| cagacgtccc caacctccgt ctggaagaca caggcagata gcgctcgcct cagtttctcc | 7200 |
| caccccaca gctctgctcc tccacccacc caggggggcgg ggccagaggt caaggctaga | 7260 |
| gggtgggatt ggggagggag aggtgaaacc gtccctaggt gagccgtctt tccaccaggc | 7320 |
| ccccggctcg gggtgcccac cttccccatg acgcgtgctg acacctggc ttcagacttc | 7380 |
| gccttctcac ccccaccagg tgggggtgat gggtcagcag ggctggagcc gggctgggtg | 7440 |
| gatcctcgaa cctggctaag cttccaaggg cctccaggtg ggcctggaat cggaccaggc | 7500 |
| tcagaggtat tggggatctc cccatgtccg cccgcatacg agttctgcgg agggatggca | 7560 |
| tactgtggac ctcaggttgg actgggccta gtccccaag ttggcgtgga gactttgcag | 7620 |
| cctgagggcc aggcaggagc acgagtggaa agcaactcag agggaacctc ctctgagccc | 7680 |
| tgtgccgacc gccccaatgc cgtgaagttg gagaaggtgg aaccaactcc cgaggaggta | 7740 |
| agtgaaggga cttggctggg ctggcagagg cagcagtgaa gggaattggg aacatgtagg | 7800 |
| gtagccaccc tgcctgccaa aggtggtgat ggctgccggg cctcctgaga agcacgacgc | 7860 |
| agtgtggact agaacccaga attgcaagaa tcagaaaccg gcctggattg tttcggcctg | 7920 |
| gcccttgtca tgtaggtcac ctaggcctgg cctgtgtccc gacacttgct tcatgccatc | 7980 |
| actgtctgta caccagtgat gcgtgaaaat cagccccccc caaaaaaaaa aaacatatca | 8040 |
| gcccctctgg ggacttggat cacagtcgga cccaggaact tggccttaag gttaggcatg | 8100 |
| gctgggggg taaaaaatgg tgcttatcct ggagttattg ttactgaaga ggttgggtgt | 8160 |
| gactggctgc tgataggagc tcttgttttgg gccatgtgtg gagtagggct caccttcagt | 8220 |
| caagtttacg gcctgtctac tttagcctca gactccatga gtcaccttta cacgagcaga | 8280 |
| cccttgtagt gcctgaggtg cagatctgat cgatttcagc cttctacct ttccttgtaa | 8340 |
| acaagaaagg gacacccttg ggtagggag ttttatctcc aggccatctt aagatcattc | 8400 |
| tgtgagtgca cgggccttgc ttagtgtctg atggcctaca gccagcactc tggagcaagt | 8460 |
| gtaagcaatt agccttaaga acaaggtgcg agtggatacc gatgcccgcc gggagttccg | 8520 |
| acagcttagc gattgttgta gcaggagtcc cctccctaag tgccagtttc tgtgttatct | 8580 |
| caggtcctgt atgccgccgg gagtccccta ggaaggcatt aatagtttat ctcacatctt | 8640 |
| aaatggccct taatgaagca agagatttga accttagtta agctaatccc aaatcctcaa | 8700 |
| aataggattt agaaaagcca aagacactgc tgagggcgat tacaagtttt ggtcttttga | 8760 |
| ggagcagttg gagatgaaag tctgtctgaa gccgagagaa tccttttcca ttgaaatggc | 8820 |
| attgaggtgt gcctcactgg ctgctgcttc tgtctgtgcc ctgggttggc cagcctttgt | 8880 |
| ggagcacctc agccctccat cctggacctt tgctccaaca acctgctcct cttccgccct | 8940 |

```
caaggctgac ttgcatctcc ccagatgact gcctccattt ctgtcttctg ttagagacag    9000
aaaagcctga gaaaccgaca gccattttgg ggggggggtc cggttcacac gctgcaactt    9060
agaaagcaca ctcaactggc catctgttat accctcccca cctggtccca accatcactg    9120
tgtattactg agaagaaggc agccttagcc acaccctcga gtgcccctgc cgttctattg    9180
ctcatacatc gattgatatc cctgtttcaa ctttgaaaaa aaaaaatttt ttttttttg    9240 tggtgtgtgc atgcctgcta ctgtacacct gtgggcgtca gaggtggtcc tctgcaccct    9300
ccggccagta ccgcatccag ggtgagtcag atgatttcct gtggtttggg cctcaaggct    9360
tctcacctcc agaggcttct agcctgctgc cttgctttct ctgtcgcact ctagtacagc    9420
aggagttttc ttcgcactcc ggagtgttgt cagctcctgg ggcatggaca tttggctact    9480
tagagtgtgc tgtgtaggtt ttcatttaga gctgaacaga gggatggatc ttattacccc    9540
agcccttgag acactgaggc aggagagctt cctagtgagt ccctgtttca atatcttcac    9600
taatactgtg tcatactttg ggactttctt tcttcctttc tttctttga ttttttttt    9660 ttttatatga gtacagtgta cctgtcttca gacacacacc agaagagggc atcagatcct    9720
actacagaag gttgtgagcc accttgtggt tgctgggaat tgaactccgg atctccggaa    9780
gagaagtccg tataccaact tctgtattag tcagggttct ctagagtcac agaacttatg    9840
gacagtctct agatagtaaa ggaatttatt gatgacttac agtcggcagc ccaattccca    9900
acaatggttc agtcgcagct gtgaatggaa gtccaaggat ctagcagtta cttagtctca    9960
cgcagcaagc aggcgaagga gcaagagcta gagcttaact gctgagccat gtgtttcttg   10020
agtaaaggga ttacatgctc gttcgtctgg tcaattctgc agccttaaaa cttcttcaga   10080 ataggggtgac atttttgtcct cagtggggcg ttttgagta atctgtgagc agataggaac   10140
ttgctggggt actgcacaga actctgggta gtgtggtact gtagatggct aggttctggg   10200
gggggaaaga gccatctatg tcacctagga atagagtgaa taacatttat ataatcagac   10260
cagcccttga ggaggctgag atcttttcat ggggcaccct agggtcacag tcccagctgg   10320
tgtgactctg acaagtctgc ctttctcact acagtcccag acatgaaaag ccctgcagaa   10380
ggagctagaa cagtttgcca agctgctgaa gcagaagagg atcaccttgg ggtacaccca   10440
ggccgacgtg gggctcaccc tgggcgttct ctttggtggg tctccccag catgttctga   10500 tctcacggct cttaatgtag gcgcaagggg gtggggcatc ttaggagctg cttctccaca   10560
ggtaagggag gattagacgc ttgtagcttg aactgtcaga ggtgggggct tgggctccct   10620
tcttgctgcc tcactcactc tgtttgatcg gccttttcagg aaaggtgttc agccagacca   10680
ccatctgtcg cttcgaggcc ttgcagctca gccttaagaa catgtgtaag ctgcggcccc   10740
tgctggagaa gtgggtggag gaagccgaca caatgagaa ccttcaggag gtgaggagtg    10800
gcaggatgtg tgcaatgtct gccaggcaca gtcccttctg ctgcttccat tcctggcttg   10860
aaactcctcc ctctccaacc ggagctcgca ggagaagttc tgtgtcctta ttctgctgct   10920
atgaattgga atccagagcc ttaacatttg ctaatcaatc aggctctctc cttctgagtc   10980
accctctgcc cccaccagcc tgacaatggt ccctccccag aacccgtct agtgctggtg   11040 aaggctcaga cctaggtcta ccagcccctt ccagagcccc tttcagtaac cctggctct    11100 ggggccacat ccagtcaatg ctcccttagc acaatccctt agcggtttgt tcttcagtcc   11160
catctcaagg tgggctgtt gccaagtcaa atactaaagt tgctcttgtc gcccccatct    11220 tccccctgccc agatatgcaa atcggagacc ctggtgcagg cccggaagag aaagcgaact   11280
agcattgaga accgtgtgag gtggagtctg agaccatgt ttctgaagtg cccgaagccc    11340
```

-continued

```
tccctacagc agatcactca catcgccaat cagcttgggc tagagaagga tgtgagtgcc    11400
aagatcctgc cctgtggtac ctggatgttt ccctgttccc attccccacc ccccccaccc    11460
ccccaccccc accgccgcca ccgctgactg cagcatccca gagcttatga tctgatgtcc    11520
atctctgtgc ccatcctagg tggttcgagt atggttctgt aaccggcgcc agaagggcaa    11580
aagatcaagt attgagtatt cccaacgaga agagtatgag gctacaggga cacctttccc    11640
agggggggct gtatcctttc ctctgccccc aggtccccac tttggcaccc caggctatgg    11700
aagcccccac ttcaccacac tctactcagt ccctttcct gagggcgagg cctttccctc    11760
tgttcccgtc actgctctgg gctctcccat gcattcaaac tgaggcacca gccctccctg    11820
gggatgctgt gagccaaggc aagggaggta gacaagagaa cctggagctt ggggttaaa     11880 ttcttttact gaggagggat taaaagcaca acagggtgg ggggtgggat ggggaaagaa     11940
gctcagtgat gctgttgatc aggagcctgg cctgtctgtc actcatcatt ttgttcttaa    12000
ataaagactg ggacacacag tagatagctg aattttgttt tccttcagtt cctagagagc    12060
ctgcggttgg agaaagccag taatggattc tcaaacccca ggtgatcttc aaaacaggcg    12120
ccattgaaac cattggagtt ccacaaaatg cccaggata gttggggttg agcccaacc      12180 tatagaggaa ggcattgcat attcgccatc ctagaggcgg taagtctctg ctagctgatg    12240
gacatcacct catagccatt gtctggcagc cgccttcttt cctcttgtca ctctgggagt    12300
tctggtgggc ttatacttta aaaaaagag tttttttggg ggggttaaga tttatttat     12360 ttatatgggt acactgtagc tgtcttctag acacaccaga agagggcatg ggatcccatt    12420
acagatggtt gtgagccacc atgtggttgc tgggaattga actcaggacc tctggaagag    12480
cagtcagtgc tcttaaccgc tgagccatct ctccagccct caaactcttt ttttcttt      12540 ccttcaagat gagttctgtg tagtcctggc ggaccaggtt ggcctcagat cagcctgcct    12600
ctgcctccgc agtgctgaga ttaaaggccc gtgccactct aggctaaatt gttatgcttc    12660
tattctagct gatgaccacc ttttttgggc gtagtagtgc tgggagtagg gtctgtacac    12720
atgtctacaa tgccagaata ggtcaaaggc tttagatctc aaggaactgg atttatagag    12780
agttgggagc agccatgtag gttctgagaa ccaaacctgg gtcctctgca agaagagcca    12840
ttggcttttt gtttttgttt gttttgagac atttctcggt gtagccctgg ctatctggaa    12900
ctctgtaggc caggctgtcc ctgaactcag atccagtcta tccatccctg ccttccaaga    12960
gctgggatta aggtcatgta ccaccacagg ccagctagcc atagctccta actgctgaac    13020
catttattta tttatttatt ttatttttttt ggttttcga gacagggttt ctctgtatag    13080
ctctggatgt cctggaactc actttgtaaa ccagtctggc ctcgaactca gaaatctgct    13140
tgcctctgcc tccccagtga gtgctgggat caaatgcgtg cgccaccact cccagcttaa    13200
gtctttattt tttaaaatgt tatttatttt ggggctggtg agatggctca gtggttaaga    13260
gcactgactg ctctgccaga ggtcccgagt tcaaatccca gcaactacat ggtggctcac    13320
aaccatctgt aatgagatct gacgccctct tctggtatgt ctgaagacaa ctacagtgta    13380
cttacatata tatataataa ataaattaaa aaaaaaaag agaggaggag ccaagcagct    13440
cctttagaaa aaaaaaagt tatttatttt atgtatttga gctgtcttca gacacaccag     13500
aagagggcaa tggatcccat tacagatggt tgtgagccac catggttgat gggaattgaa    13560
ctctggacct ctggcagagc agtcagtgct cttaaccgct gagccatctc tccagccccc    13620
aaagccaagt cttaaagcat ttttgctgct gaatgtcagc cctaccagat ctctgcctcc    13680 ctccccctccc ctcccccccag tatctcatga agaccaagct ggcctggaca cagtaagtat    13740
```

```
gtgcatattt atgtgtgaag attgtcacaa tgtgaggaaa aaagttggtt ccctccatgg   13800
tgtgggtcct gtgggtcaag tccaggtcgc taggcttggc agcaagtgcc ttgactcata   13860
gtcttctcct gcccaactcc atgcttggtt tccacgagcc cctgtgctat ggagaattcc   13920
atctccaggc ctcaccaaat ctaatctccc catcctttga aaagcagact tagattcaac   13980
gcaagtggat gaaacagttt attctttatt tgggaataaa gactaagctc tgaaaagcta   14040
gtcccagaga ctcagctggt ggtgatacta gctagcggtg gcatgaggat gccttgggaa   14100
tgtgctctgg gtccttcagg gtgctttagc cgatgccatt caagaacatg agtagggtta   14160
gggtattgtg gcagagcact tgcctggtat atgctggctt cagcaaaata aaaccatacc   14220
ttctaggaat ggtttctggg accggtgctc taactgcagg tatcctggca tccatggagg   14280
caaggctta ttccttgtga ctgggcttgt agctcactgg aaacttggag gctgcaacat   14340
ctttggcagg aaaccatctt ttctgtcact tcatttgcaa gcattctcca gccttgagtc   14400
agtcttagc aatggacctt tccctgtggt cattcccttt ggagaaagac attcctcaaa   14460
gtccatggta actttgaatg agtgttttgc atgtacacat gcgtgagtgt gcatgcgctc   14520
tcacacacgc acgcacatgc acgcgcgtgc acacacacac acacacacac acacacacac   14580
acacacacac acacacactg cttcagcccct taggagccat tcttctatta ttatgtttga   14640
gtgctctgcc tgaatgtgca cctgcaggcc agaagagggc atcagatccc ttttagagat   14700
ggtcacaagc catcatgttg ttgctggaaa ttgggacttc tggaagagca gccagtgtac   14760
ccttaattgc tgagccatct tactgcccaa gatacattct tacactgtgc ctgaccctga   14820
gccacatctg tgtcctgact gcaaagtcaa gatgccatta tggcatcctg gatgctatag   14880
ccagtgcagg ccagagggta ccagatgtca cagccatcac accaacccag gctctgctct   14940
ctagcaaaaa gaagctggac aggactccct aagggagtga gtgttcctga gaaaccctttt   15000
gagtaacttg cctctgggta actggtagcc agaacaggag gctaagactg ggatatagga   15060
acttggagat tagggatgtt aagtagagca tacgcatagc acaaaagata cttggctttg   15120
gatatgagct gttgacgcct tcaatccatc acaactccca ttctgaatgc tctatcccga   15180
ctacatgagg gatttgaggc tagcctggat tacacagtga gaccttgtat taaaaaagag   15240
ttgggtgtct cctccagaga ggatctgggt ttgaacctca gcacctacat agtggctagc   15300
aattatccct ccagttccca gagaacccag tgccctcttc tggcttctgc cggtattgca   15360
tgcaagtgtg ataccccaatc atgcaggcaa acaaagcagc cttgaattga cctgctctcc   15420
tctagttttg agacagtgtt agtatggttt tttatgtata gtgctgggac tccaaacatg   15480
ggcaagtcag gtgcttgcta ggcagtgctc ttctagtgag acatctcttt gttccctgtc   15540
tcccagattg ctttgtatag tctagtccta accattgttc ccacatagta gcttgtcatg   15600
catttatggg tgaaagctaa cctgggtgtc tgctgtgccc gtgcaccccc cttccctgcc   15660
ttctaagacc tcagtctgag gctgttcaaa gatctagaat tcaaggtgct gacaggtgac   15720
cccacttacc cactggctat cagagcagct ttctccaccc ggagcctctt cctgggctcc   15780
gtcaggacgc acagggggcc tggggagacc tcatcatcta gctctgccaa cactttatga   15840
gctgatttcc tccggtttct tgtgggtgga gcaggcgaaa cttgcgcttc cccatgctga   15900
gagggaatag ccaggccctg tggcctgcca ccaccacggg agaaggtgag aggctgggcc   15960
tggagtttgc tgaggctgcc gatggaattg agaatcagtg tggccttggg ggcagaggag   16020
agagtgctga gtgcctctg aggtgcccct tgggggggca gcataggttg gaaaccgccc   16080
ccagcttctc ccttagaccg agggacggtt atggctgcaa agtcctgagg tttaacccgg   16140
```

-continued

```
acttgttgaa acatgaagta gaactctgag gaggagctgg ttcctgcttg accttggggg    16200
ccaaaggtca gaaggtcacc atcactcaac tccagtctgt ggcctcttgg aagtcggaca    16260
ttattgacca aagtccctgg tgataatgag acagacataa gacaggtgac gagaacagga    16320
acagacttgt agtcagaatt aacatgatcc gaattcgttc cctttagtga gggttaattc    16380
cgcggccgc                                                            16389
```

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2

```
gcaagctgac cctgaagttc atc                                            23
```

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3

```
tcaccttgat gccgttcttc tg                                             22
```

<210> SEQ ID NO 4
<211> LENGTH: 17503
<212> TYPE: DNA
<213> ORGANISM: Murine

<400> SEQUENCE: 4

```
gcggccgcgt aatacgactc actatagggc gaagaattcg gatctcatta cgggtggttg     60
tgagccacca tgtggttgct gggatttgaa cttcggacct ttggaagagc agtcgggtgc    120
tcttacccac tgagccatct caccagcccc tggattataa attcttattt gtacagtttt    180
tgttgttggt tttgtttgtt tgtttgtttc aacacttggg attgaatcca gggtcattgg    240
agtgtttggc ctgggttctg ctgctgagcc acactccata tacttgcatg gattgtgtct    300
tttattctat gtggtggtgg tggtggtggt ggtggtggtg gtggtggtgg tggtggtggt    360
ggtagaggga actcacccag cccacctcct ctggtttcac tcctccacac acacccttca    420
tccctgtcct taccccctgc cagtaagaaa ctccacagga tgtctctcta ggagtctgag    480
aaaaaagcac taagagaaca agctgttttgt ttttggggt ttttttttggg ggggtggggg    540 ggggagttag aactcaggaa atcagaacag ggctaggtgt ggtaatgaat gacatagatc    600
tagtcactca aaggctgtgt acctctgaag ttgagactag cctggtttat ataaaaagta    660
acctggtcta tataaaaaat tctaagttac gccgggcgat gatggcacat gcctttgatc    720
ctagcacttg ggaggcagag gcaggcggat ttcgaagttt gaggccagcc tggtctacaa    780
agtgagttcc aggacagcca gggctacaca gagaaaccct gccttgaaaa caaacaaaca    840
aacaaacaaa aaaccaaaaa caaccaaaac aaacaaacaa aaaaccccca aaaccaaaac    900
aaaacaaaac aaaagttct aagctatgta gaactcttgg ggcactcgtg atcaaagtct    960
aagcattgaa aatctctaaa tgccaggctt ggtggcgcac gcacttaata ccagcacttg   1020
ggaggcagag gcaggcagat ttctgagttc gaggccaacc tggtctacaa agtgagttcc   1080
atgacagcca gggctacaca gagaaaccct gtctcgaaag acaaaaaaaa aaaaaaaaaa   1140
```

-continued

| | | | | | |
|---|---|---|---|---|---|
| aaaaaaaaaa | aatctctaaa | caagccctat | caatcttccc | ttgggggtat | ggactgttat | 1200 |
| ctcttcatca | taagaggaaa | gcgaataggt | ggtgtgaagg | aggtctttgg | tggtgcagga | 1260 |
| gggagccact | ggctgcaggg | gacacagggt | acagcatggc | tccttagttg | acatctgct | 1320 |
| tgacagaatg | agtgtctatc | tatctgtgga | cttgggaatc | aaccccaggt | attccaggag | 1380 |
| gtaagaagaa | ccactctctg | aaccaggtg | gtcttttgag | ccaccagaaa | aaacatccac | 1440 |
| catgtaattg | taaccaagta | accagtcata | accccctgca | acagcgccca | ggagacttt | 1500 |
| gaatctgaaa | caagcagaac | cacagagagg | gggaggaaag | gttatcctga | cccagagagg | 1560 |
| caaatcctct | ctggaacccc | gggagctagg | tcagatgcta | agggcatttg | tggggagggc | 1620 |
| tgggagagaa | gggccctagg | ctagcagcag | gtcctccttc | cctttaacct | ctggccatgt | 1680 |
| tgggtaggga | ctctccttga | caaacctgat | aaccaggagt | tcatttccga | gcacccacac | 1740 |
| agtggaagaa | gctagcccat | cgcctaaagt | tgccttttg | ttctcttttt | ctctctctca | 1800 |
| cacaaatttt | taaattttat | tatttattta | ttgacataat | ttctctatgt | atcccaggct | 1860 |
| gtctcagaac | tcactttgta | gaccaggctg | gcctcaaact | tagagatgct | cctacctctg | 1920 |
| cctcctgagt | actaggatta | aggatatcca | tcacaacacc | taactgtaat | aaaaatttca | 1980 |
| atttttttt | ctctcttagc | ctcagctgca | atcacctctt | ttagccagta | tacctgcagg | 2040 |
| agctccagtc | cataggcggg | ctctcctaat | gcctgaattt | gactctcaaa | gtgcattcac | 2100 |
| ttcctctcat | tacagctctt | ctgcagactc | ttttatatca | ggaatctcaa | aacttgggtt | 2160 |
| gggcatggta | ctcgcctta | atcccaggag | gtggaggcca | gcctggtgta | caaagtgagt | 2220 |
| tctaggtcag | gcaggactgt | aatgtctact | ccttacatga | acaggatagg | gcctggcggg | 2280 |
| gagagagggg | ggaagctagg | tgggagtaag | ggtggaaacg | ggcaatcgtg | tcaatggaag | 2340 |
| aagtaaatga | tcaagacaat | aggtctgttc | acagcattag | aaccacccaa | atggtcattt | 2400 |
| ggcatcggag | tcctctccct | cctcccaatc | ccccccccat | ttgcttatct | atttattttt | 2460 |
| attttatgta | tgcaagcatt | tttcttttt | ctttttcttt | ctgggttttt | cgagacaggg | 2520 |
| tttctctgtg | tagccctggc | tgtcctggaa | ctcactctgt | agaccaggct | agcttcgaac | 2580 |
| tcagaaatct | gcctgcctct | gcctcccaag | tgctggaatc | aaaggcaagg | gccaccacac | 2640 |
| ctggcgcaag | catttttcaa | agatgtattt | gtttatatat | gtgagtacat | tatctctctc | 2700 |
| ttcaggcaca | ccaggagaga | gagagagaga | gagagagaga | gagagagaga | gagagagaga | 2760 |
| gagagagaat | cagatcctgt | cacagatggt | tgtgagtcac | caagtgggag | ctgggatttg | 2820 |
| aactcaggac | ctctggaaga | gctgtcagtg | cacttaacct | gtgagccatc | tctccagtcc | 2880 |
| ttttcctctc | tgtttttttt | tttttttttt | tttttttttt | gacacagttt | aaccatgtag | 2940 |
| cttaggctaa | tcttcagttt | gctgtgcctc | agcttctgag | tgtccacttg | ggattgcagg | 3000 |
| agtttgccgc | cttgctcagc | ttacagcttg | ggatgctctt | ctcacagaca | tccacgtact | 3060 |
| agtactgaaa | gacaaagaca | aacaccggtt | tgcttgcaaa | ctgctcaagt | cttgtctagt | 3120 |
| ttgattaggc | ttgagaggag | accttgccag | ctttcccaag | aagactgtgt | ggaggttggc | 3180 |
| ggtagaaggt | ggggtacaga | agacttgctt | tcatctcaca | aggtgcccca | cccatctctc | 3240 |
| taacgcccaa | ttttctttta | cagaggcaca | gggacaactc | cctaccccga | cccatgtgga | 3300 |
| gtgagaaggg | caggaggatg | catgggaata | gggctgtagt | tttcttttca | agttggaaga | 3360 |
| aaatggagag | ttaggccagg | gaaggtagtg | acaccccct | ggggtgtcac | acacacacac | 3420 |
| acacacacac | acacacacac | atacacacac | agggaattct | agcactggtg | gtgtgagcaa | 3480 |
| gtaggtagct | atatgtagta | atataacaag | atttattttg | ctgagagtca | tcacataagg | 3540 |

```
ttcacactct aagccagcca ggtggtggtg gtggcacatg cctttaatcc cagcacttcg    3600
gagacagaga caggaggatt tctgagttcg aggccagcct ggtctacaaa gtgagttcca    3660
ggatagccag ggctacacag agaaaccctg tctcgagaga aaaaaaaaaa aaaaggttca    3720
cactctgtaa attcctaact aatgtctcat tcctgtctcc ccacagctgc tcacctatgt    3780
gacatatttt agcagaaggt caggtccact ctcttaatct cttaagagtg tctgtgattt    3840
gagggacagg atcctagcgg ggagactctc cacctcaaag gcagatcaag gtggctggtt    3900
atcttgaatg agtgatgtcg tggggttctg gttatcaggg gcagccttgg gtgtagtggt    3960
gaagccattt ctgcaagtct aaaaggcatt tggacactgc tcatcagaac tgggaaggca    4020
agaggatcag aagttcaagg gccttcttgg ctacgtagag tttaggggca gcctctgcta    4080
catgtaaatt tgtctcagaa gaaaaaagga aacgggcagt agtggcgaat gcctataatc    4140
ccagcacttg ggaagcagag ggcaggctga tttctgagct caaggccagc ctggtctaca    4200
gagtgagttc caggacagcc agggctacac agagaaaccc tgtctcagaa agaaaaaaaa    4260
aaaaagggag aaatagaact catttatttc aaagggagca ggcacattcc gcaagccttc    4320
tgttctgctg gtgaccctat tcctaccttc agcttctaga cttgtttttt tcttttaatt    4380
tttattgtat tgtgtgtgtg tgtgtatctg agtgcaatat caatatcgaa cctctggaga    4440
tcaaatgctt ctttgaaatg gaccccaggg atcaaatcca tggtcgttag gctcagcaag    4500
tgtggttact tgctgagctg tcctcaggtt cctctcaggc ctcccctcaa gtctcccct    4560 ccaacccccc cccccctcc tgccccctgc aagtcttttt gattaggcaa gaaaccaag    4620 acaaggaaag ggagatgcag ttagctaagg aatctatgcc agccagagaa actacctcct    4680
cccttccaga acatctggat ttgggaagag acgttgctgg tcccagggcg gctgggggtt    4740
ggggttgggg gaggggatg ctaaccagca aggaagctgt tcctggctgg ggcaggcctg    4800
actgagctca tgtcgctgaa actcctcatt tctccctatg gcttcatagg gagacccagc    4860
ctggatgcta acacgagtga tttccctgct ctagtctagt gtcctccgtg agtccattta    4920
actgatcacc cagtctgtga ggaggtggct gaactcacag taagaaagct gtggggtca    4980 acgcctattg tttgtttgtt ttgttttaga caaggtctcc tgctgaggct ggctcaagct    5040
ggcctggagg actcttgtgt ttaaggctgg ccttaaattc tctttaaaag aaaatcatgt    5100
gtatatatgt gtgtccatgt aactgcagat gaccacagca gccaagagat ttctgttctc    5160
ctagctgtaa accacccaat atgggtgcta ggaacagaat tttaaagggg tcctctgaaa    5220
gagcaatgta cactcaaatg ctgagttctt tcccagcccc tagccttgga cctttgttct    5280
tatcacttcc aacgcccaag ggcaggcatt ataggtgtgg cattccgcat ctggcttccc    5340 aggataccctt ttcatgctgg tggaccatct ctggctgggg acgtgtgggc ttctctgctg    5400
tctttggttc tccagacaga actccgagac agatcttgac ttggttctaa aatacaggtg    5460
gtttgtggca agttaacgaa ttttagctca aatttggggt atttaagata ccatggtgac    5520
tcttttttgt ttgttttct ttctttcttt tttttttta aaaagattta tttattattg    5580
tacgtaagta cttcagacac cagaagaggg tgacagattt tttttttttt tcgagacagg    5640
atttctctgt gaagccctgg ctgtcctgga actcactctg tagaccaggc tggcctggaa    5700
ctcagaaatc cacctgcctc tgcctcccaa gtgctgggat taaagccatg agttgggacc    5760
gcacccggcc caaagtgact cttaaagggg gcagagtggc acatattttc aatcctagca    5820
ctcaggaagc aaaggctggt ggatctctgt gagttcaagg ccagcctggt ctacagagtg    5880
agttccaagc catctaaggc tatgtaggga accccttgaat caaacccaaa agttagtctg    5940
```

```
atgattttct aagacccagg aggcaagaaa ctggatcaga tgagccaaca ggtctgctgt      6000
cccatctcca gggccaccag gctcacagct cgggaccagg ctagggcaca tctgtttcaa      6060
gctagttcta agaagacttg ggacttcaga caaagttgct gttaaggact gtattatact      6120
ctaggcacgc ttagggctaa cctggttgca aagccagtca ctaggcagtt aaaggactca      6180
gaatatgtct cttgtcctgg ccagtgagtc accaaaagag aaatcacaat ccataagaca      6240
aggttggtat tgaatacaga caggactgct gggctgcagg catacttgaa ctgtggtgga      6300
gagtgctgtc taggccttag aggctggccc tgggaggaac tgggtgtggg gaggttgtag      6360
cccgaccctg cccctccccc cagggaggtt gagagttctg ggcagacggc agatgcataa      6420
caaaggtgca tgatagctct gccctggggg cagagaagat ggttggggag gggtccctct      6480
cgtcctagcc cttccttaat ctgctattga ggaagctttg tgaacttggc ggcttccaag      6540
tcgctgcctt tatttaggtc ttccaactaa cctatggcac tgttccacaa tgaatgtata      6600
gaaattggga ggtgagcatg acagagtgga ggaaacggaa gattcatgga gagggccaga      6660
gagatggccc ctcagccacc ctgggggatg acttggaccc atgtggtaga aggaggggac      6720
ttccacacat gtgctatgtg tagctgtgtg taggtacata cacaccctta aaataaaacg      6780 caatttttt ttcaaagtct cagggtgaat ttggtgaagt cgatgaagct gaggcaggag      6840
aattatcagg agttcaaggg cagcttgttt tatagaaaa ggttccatct ctacctgatg      6900
aagactacca tcaagagaca ccccgccccc cagggcacc tagagccact gaccctagcc      6960
aacagctcag gcgggctggg cccaggctca gaactctgtc ctggctatgt acactgtggg      7020
gtgctctggg cttttgagg ctgtgtgatt caccctgggg ccttcgttca gagcatggtg      7080
taggagcaga cagacaaaca ccatccctg cagacaggca ctctgagggc tattctcttg      7140
caaagataac taagcaccag gccagtaatg ggatcctcag actgggccca gaaaaccact      7200
ctagggaagt tcagggtagg ctctctgcac cccctcctcc taatcccgtc tccttagtgt      7260 cttccgcca gcacaggaat ggggagggg tgggtgacga ggatgaacac cggagtccct      7320
ggaggaaggg aagcagggta tctccatctg aggctctgtc tttgaggaga ggtggagagc      7380
tggggaagtc ttgtgtgagg ggattgggc tcaggagggg gttggggagc aggaagttgt      7440
ccccagggga gccatcctgg cccattcaag ggttgagtac ttgttaggg ttagagctgc      7500 cccctctggg gaccaggatt gtccagccaa ggccattgtc ctgccccctt ccccagtcc      7560 ctcccaggcc cctttgaacc tgaagtcaga tatttcttct ctctacccac ctcccacccg      7620
ttgggtttct ccacccagga actaggctgg aagcctggga tgaggaggtg gggggaggga      7680
gaactgagaa tcttgaggaa agaggccccg gccttaactg tgaggggatg gagcctgggt      7740
gcaggtctta tggggttgg ggggtggtta gtgtctaatc taccaacctg gacaacacaa      7800 gatgaatac tgtgctctga aaacgcagag ccagcacttc tctggggtct ctggggacat      7860
atctggttgg ggctcggggt cccatggtgt agagcctcta aactctggag gactggaggt      7920
gcaatggctg tcttgtcctg gccttggaca tgggctgaaa tactgggttc acccatatct      7980
aggactctag acgggtgggt aagcaagaac tgaggagtgg ccccagaaat aattggcaca      8040
cgaacattca atggatgttt taggctctcc agaggatggc tgagtgggct gtaaggacag      8100
gccgagaggg tgcagtgcca acaggctttg tggtgcgatg gggcatccga gcaactggtt      8160
tgtgaggtgt ccggtgaccc aaggcagggg tgagaggacc ttgaaggttg aaaatgaagg      8220
cctcctgggg tcccgtccta agggttgtcc tgtccagacg tccccaacct ccgtctggaa      8280
gacacaggca gatagcgctc gcctcagttt ctcccacccc cacagctctg ctcctccacc      8340
```

-continued

```
cacccagggg gcggggccag aggtcaaggc tagagggtgg gattgggagg ggagaggtga      8400
aaccgtccct aggtgagccg tctttccacc aggcccccgg ctcggggtgc ccaccttccc      8460
catgacgcgt gctggacacc tggcttcaga cttcgccttc tcaccccac caggtggggg      8520 tgatgggtca gcagggctgg agccgggctg ggtggatcct cgaacctggc taagcttcca      8580
agggcctcca ggtgggcctg gaatcggacc aggctcagag gtattgggga tctccccatg      8640
tccgcccgca tacgagttct gcggagggat ggcatactgt ggacctcagg ttggactggg      8700
cctagtcccc caagttggcg tggagacttt gcagcctgag ggccaggcag gagcacgagt      8760
ggaaagcaac tcagagggaa cctcctctga gccctgtgcc gaccgcccca atgccgtgaa      8820
gttggagaag gtggaaccaa ctcccgagga ggtaagtgaa gggacttggc tgggctggca      8880
gaggcagcag tgaagggaat tgggaacatg tagggtagcc accctgcctg ccaaaggtgg      8940
tgatggctgc cgggcctcct gagaagcacg acgcagtgtg gactagaacc cagaattgca      9000
agaatcagaa accggcctgg attgtttcgg cctggccctt gtcatgtagg tcacctaggc      9060
ctggcctgtg tcccgacact tgcttcatgc catcactgtc tgtacaccag tgatgcgtga      9120
aaatcagccc cccccaaaaa aaaaaaacat atcagcccct ctggggactt ggatcacagt      9180
cggacccagg aacttggcct taaggttagg catggctggg ggggtaaaaa atggtgctta      9240
tcctggagtt attgttactg aagaggttgg gtgtgactgg ctgctgatag gagctcttgt      9300
ttgggccatg tgtggagtag ggctcacctt cagtcaagtt tacggcctgt ctactttagc      9360
ctcagactcc atgagtcacc tttacacgag cagacccttg tagtgcctga ggtgcagatc      9420
tgatcgattt cagcctttct acctttcctt gtaaacaaga aagggacacc cttgggtagg      9480
ggagttttat ctccaggcca tcttaagatc attctgtgag tgcacgggcc ttgcttagtg      9540
tctgatggcc tacagccagc actctggagc aagtgtaagc aattagcctt aagaacaagg      9600
tgcgagtgga taccgatgcc cgccgggagt tccgacagct tagcgattgt tgtagcagga      9660
gtcccctccc taagtgccag tttctgtgtt atctcaggtc ctgtatgccg ccgggagtcc      9720
cctaggaagg cattaatagt ttatctcaca tcttaaatgg cccttaatga agcaagagat      9780
ttgaaccttg gttaagctaa tcccaaatcc tcaaaatagg atttagaaaa gccaaagaca      9840
ctgctgaggg cgattacaag ttttggtctt ttgaggagca gttggagatg aaagtctgtc      9900
tgaagccgag agaatccttt tccattgaaa tggcattgag gtgtgcctca ctggctgctg      9960
cttctgtctg tgccctgggt tggccagcct ttgtggagca cctcagccct ccatcctgga     10020
cctttgctcc aacaacctgc tcctcttccg ccctcaaggc tgacttgcat ctccccagat     10080
gactgcctcc atttctgtct tctgttagag acagaaaagc ctgagaaacc gacagccatt     10140
ttgggggggg ggtccggttc acacgctgca acttagaaag cacactcaac tggccatctg     10200
ttataccctc cccacctggt cccaaccatc actgtgtatt actgagaaga aggcagcctt     10260
agccacaccc tcgagtgccc ctgccgttct attgctcata catcgattga tatccctgtt     10320
tcaactttga aaaaaaaaa ttttttttt tttgtggtgt gtgcatgcct gctactgtac     10380
acctgtgggc gtcagaggtg gtcctctgca ccctccggcc agtaccgcat ccagggtgag     10440
tcagatgatt tcctgtggtt tgggcctcaa ggcttctcac ctccagaggc ttctagcctg     10500
ctgccttgct ttctctgtcg cactctagta cagcaggagt tttcttcgca ctccggagtg     10560
ttgtcagctc ctggggcatg gacatttggc tacttagagt gtgctgtgta ggttttcatt     10620
tagagctgaa cagagggatg gatcttatta ccccagccct tgagcactg aggcaggaga     10680 gcttcctagt gagtccctgt ttcaatatct tcactaatac tgtgtcatac tttgggactt     10740
```

```
tctttcttcc tttctttctt ttgattttttt ttttttttat atgagtacag tgtacctgtc    10800
ttcagacaca caccagaaga gggcatcaga tcctactaca gaaggttgtg agccaccttg    10860
tggttgctgg gaattgaact ccggatctcc ggaagagaag tccgtatacc aacttctgta    10920
ttagtcaggg ttctctagag tcacagaact tatggacagt ctctagatag taaaggaatt    10980
tattgatgac ttacagtcgg cagcccaatt cccaacaatg gttcagtcgc agctgtgaat    11040
ggaagtccaa ggatctagca gttacttagt ctcacgcagc aagcaggcga aggagcaaga    11100
gctagagctt aactgctgag ccatgtgttt cttgagtaaa gggattacat gctcgttcgt    11160
ctggtcaatt ctgcagcctt aaaacttctt cagaataggg tgacattttg tcctcagtgg    11220
ggcggttttg agtaatctgt gagcagatag gaacttgctg gggtactgca cagaactctg    11280
ggtagtgtgg tactgtagat ggctaggttc tggggggga aagagccatc tatgtcacct    11340
aggaatagag tgaataacat ttatataatc agaccagccc ttgaggaggc tgagatcttt    11400
tcatggggca ccctagggtc acagtcccag ctggtgtgac tctgacaagt ctgccttct    11460
cactacagtc ccaggacatg aaagccctgc agaaggagct agaacagttt gccaagctgc    11520
tgaagcagaa gaggatcacc ttggggtaca cccaggccga cgtggggctc accctgggcg    11580
ttctctttgg tgggtctccc ccagcatgtt ctgatctcac ggctcttaat gtaggcgcaa    11640
ggggtgggg catcttagga gctgcttctc cacaggtaag ggaggattag acgcttgtag    11700
cttgaactgt cagaggtggg ggcttgggct cccttcttgc tgcctcactc actctgtttg    11760
atcggccttt caggaaaggt gttcagccag accaccatct gtcgcttcga ggccttgcag    11820
ctcagcctta agaacatgtg taagctgcgg cccctgctgg agaagtgggt ggaggaagcc    11880
gacaacaatg agaaccttca ggaggtgagg agtggcagga tgtgtgcaat gtctgccagg    11940
cacagtccct tctgctgctt ccattcctgg cttgaaactc ctccctctcc aaccggagct    12000
cgcaggagaa gttctgtgtc cttattctgc tgctatgaat tggaatccag agccttaaca    12060
tttgctaatc aatcaggctc tctccttctg agtcaccctc tgcccccacc agcctgacaa    12120
tggtccctcc ccagaacccc gtctagtgct ggtgaaggct cagacctagg tctaccagcc    12180
ccttccagag cccctttcag taaccctgg ctctggggcc acatccagtc aatgctccct    12240
tagcacaatc ccttagcggt ttgttcttca gtcccatctc aaggtggggc tgttgccaag    12300
tcaaatacta aagttgctct tgtcgccccc atcttcccct gcccagatat gcaaatcgga    12360
gaccctggtg caggcccgga agagaaagcg aactagcatt gagaaccgtg tgaggtggag    12420
tctggagacc atgtttctga agtgcccgaa gccctcccta cagcagatca ctcacatcgc    12480
caatcagctt gggctagaga aggatgtgag tgccaagatc ctgccctgtg gtacctggat    12540
gtttccctgt tcccattccc cacccccccc acccccccac cccaccgcc gccaccgctg    12600
actgcagcat cccagagctt atgatctgat gtccatctct gtgcccatcc taggtggttc    12660
gagtatggtt ctgtaaccgg cgccagaagg gcaaagatc aagtattgag tattcccaac    12720
gagaagagta tgaggctaca gggacacctt tccagggg ggctgtatcc tttcctctgc    12780
ccccaggtcc ccactttggc accccaggct atggaagccc ccacttcacc acactctact    12840
cagtcccttt tcctgagggc gaggcctttc cctctgttcc cgtcactgct ctgggctctc    12900
ccatgcattc aaactgaggc accagccctc cctggggatg ctgtgagcca aggcaaggga    12960
ggtagacaag agaacctgga gctttgggt taaattcttt tactgaggag ggattaaaag    13020
cacaacaggg gtggggggtg ggatgggaa agaagctcag tgatgctgtt gatcaggagc    13080
ctggcctgtc tgtcactcat cattttgttc ttaaataaag actgggacac acagtagata    13140
```

```
gctgaatttt gttttccttc agttcctaga gagcctgcgg ttggagaaag ccagtaatgg   13200
attctcaaac cccaggtgat cttcaaaaca ggcgccattg aaaccattgg agttccacaa   13260
aatgcccagg gatagttggg gttggagccc aacctataga ggaaggcatt gcatattcgc   13320
catcctagag gcggtaagtc tctgctagct gatggacatc acctcatagc cattgtctgg   13380
cagccgcctt cttcctctt gtcactctgg gagttctggt gggcttatac tttaaaaaaa   13440
agagtttttt tggggggggtt aagatttatt ttatttatat gggtacactg tagctgtctt   13500
ctagacacac cagaagaggg catgggatcc cattacagat ggttgtgagc caccatgtgg   13560
ttgctgggaa ttgaactcag gacctctgga agagcagtca gtgctcttaa ccgctgagcc   13620
atctctccag ccctcaaact cttttttttc ttttccttca agatgagttc tgtgtagtcc   13680
tggcggacca ggttggcctc agatcagcct gcctctgcct ccgcagtgct gagattaaag   13740
gcccgtgcca ctctaggcta aattgttatg cttctattct agctgatgac cacctttttt   13800
gggcgtagta gtgctgggag tagggtctgt acacatgtct acaatgccag aataggtcaa   13860
aggctttaga tctcaaggaa ctggatttat agagagttgg gagcagccat gtaggttctg   13920
agaaccaaac ctgggtcctc tgcaagaaga gccattggct ttttgttttt gtttgttttg   13980
agacatttct cggtgtagcc ctggctatct ggaactctgt aggccaggct gtccctgaac   14040
tcagatccag tctatccatc cctgccttcc aagagctggg attaaggtca tgtaccacca   14100
caggccagct agccatagct cctaactgct gaaccattta tttatttatt tattttattt   14160
ttttggtttt tcgagacagg gtttctctgt atagctctgg atgtcctgga actcactttg   14220
taaaccagtc tggcctcgaa ctcagaaatc tgcttgcctc tgcctcccca gtgagtgctg   14280
ggatcaaatg cgtgcgccac cactcccagc ttaagtctt ttttttaaa atgttattta   14340 ttttgggct ggtgagatgg ctcagtggtt aagagcactg actgctctgc cagaggtccc   14400
gagttcaaat cccagcaact acatggtggc tcacaaccat ctgtaatgag atctgacgcc   14460
ctcttctggt atgtctgaag acaactacag tgtacttaca tatatatata ataaataaat   14520 taaaaaaaa aaagagagga ggagccaagc agctccttta gaaaaaaaaa aagttattta   14580
ttttatgtat ttgagctgtc ttcagacaca ccagaagagg gcaatggatc ccattacaga   14640
tggttgtgag ccaccatggt tgatgggaat tgaactctgg acctctggca gagcagtcag   14700
tgctcttaac cgctgagcca tctctccagc ccccaaagcc aagtcttaaa gcattttgc    14760 tgctgaatgt cagccctacc agatctctgc ctccctcccc tccctccc ccagtatctc    14820 atgaagacca agctggcctg gacacagtaa gtatgtgcat atttatgtgt gaagattgtc   14880
acaatgtgag gaaaaagtt ggttccctcc atggtgtggg tcctgtgggt caagtccagg    14940
tcgctaggct tggcagcaag tgccttgact catagtcttc cctgcccaa ctccatgctt    15000 ggtttccacg agccctgtg ctatggagaa ttccatctcc aggcctcacc aaatctaatc    15060
tccccatcct ttgaaaagca gacttagatt caacgcaagt ggatgaaaca gtttattctt   15120
tatttgggaa taaagactaa gctctgaaaa gctagtccca gagactcagc tggtggtgat   15180
actagctagc ggtggcatga ggatgccttg ggaatgtgct ctgggtcctt cagggtgctt   15240
tagccgatgc cattcaagaa catgagtagg gttagggtat tgtggcagag cacttgcctg   15300
gtatatgctg gcttcagcaa aataaaacca taccttctag gaatggtttc tgggaccggt   15360
gctctaactg caggtatcct ggcatccatg gaggcaaggc tttattcctt gtgactgggc   15420
ttgtagctca ctgaaaactt ggaggctgca acatctttgg caggaaacca tcttttctgt   15480
cacttcattt gcaagcattc tccagccttg agtcagtctt tagcaatgga cctttccctg   15540
```

-continued

```
tggtcattcc ctttggagaa agacattcct caaagtccat ggtaactttg aatgagtgtt    15600
ttgcatgtac acatgcgtga gtgtgcatgc gctctcacac acgcacgcac atgcacacgc    15660
gtgcacacac acacacacac acacacacac acacacacac acacacacac actgcttcag    15720
cccttaggag ccattcttct attattatgt ttgagtgctc tgcctgaatg tgcacctgca    15780
ggccagaaga gggcatcaga tcccttttag agatggtcac aagccatcat gttgttgctg    15840
gaaattggga cttctggaag agcagccagt gtacccttaa ttgctgagcc atcttactgc    15900
ccaagataca ttcttacact gtgcctgacc ctgagccaca tctgtgtcct gactgcaaag    15960
tcaagatgcc attatggcat cctggatgct atagccagtg caggccagag ggtaccagat    16020
gtcacagcca tcacccaac ccaggctctg ctctctagca aaagaagct ggacaggact      16080 ccctaaggga gtgagtgttc ctgagaaacc ctttgagtaa cttgcctctg ggtaactggt    16140
agccagaaca ggaggctaag actgggatat aggaacttgg agattaggga tgttaagtag    16200
agcatacgca tagcacaaaa gatacttggc tttggatatg agctgttgac gccttcaatc    16260
catcacaact cccattctga atgctctatc ccgactacat gagggatttg aggctagcct    16320
ggattacaca gtgagacctt gtattaaaaa agagttgggt gtctcctcca gagaggatct    16380
gggtttgaac ctcagcacct acatagtggc tagcaattat ccctccagtt cccagagaac    16440
ccagtgccct cttctggctt ctgccggtat tgcatgcaag tgtgataccc aatcatgcag    16500
gcaaacaaag cagccttgaa ttgacctgct ctcctctagt tttgagacag tgttagtatg    16560 gtttttatg tatagtgctg ggactccaaa catgggcaag tcaggtgctt gctaggcagt      16620
gctcttctag tgagacatct ctttgttccc tgtctcccag attgctttgt atagtctagt    16680
cctaaccatt gttcccacat agtagcttgt catgcattta tgggtgaaag ctaacctggg    16740
tgtctgctgt gcccgtgcac cccccttccc tgccttctaa gacctcagtc tgaggctgtt    16800
caaagatcta gaattcaagg tgctgacagg tgaccccact tacccactgg ctatcagagc    16860
agctttctcc acccggagcc tcttcctggg ctccgtcagg acggacaggg ggcctgggga    16920
gacctcatca tctagctctg ccaacacttt atgagctgat ttcctccggt ttcttgtggg    16980
tggagcaggc gaaacttgcg cttccccatg ctgagaggga atagccaggc cctgtggcct    17040
gccaccacca cgggagaagg tgagaggctg ggcctggagt ttgctgaggc tgccgatgga    17100
attgagaatc agtgtggcct tggggggcaga ggagagagtg ctgagtggcc tctgaggtgc   17160
cccttggggg ggcagcatag gttggaaacc gcccccagct tctcccttag accgagggac   17220
ggttatggct gcaaagtcct gaggtttaac ccggacttgt tgaaacatga agtagaactc    17280
tgaggaggag ctggttcctg cttgaccttg ggggccaaag gtcagaaggt caccatcact    17340
caactccagt ctgtggcctc ttggaagtcg gacattattg accaaagtcc ctggtgataa    17400
tgagacagac ataagacagg tgacgagaac aggaacagac ttgtagtcag aattaacatg    17460
atccgaattc gttccctttta gtgagggtta attccgcggc cgc                    17503
```

US 7,704,736 B2

COMPOSITIONS FOR THE DERIVATION OF GERM CELLS FROM STEM CELLS AND METHODS OF USE THEREOF

CROSS REFERENCE TO RELATED APPLICATION

This application is a 371 application of PCT/US02/36260 filed 12 Nov. 2002, which in turn claims priority to Provisional Application 60/338,329 filed 9 Nov. 2001. Each of the above identified applications is incorporated by reference herein.

Pursuant to 35 U.S.C. §202(c), it is acknowledged that the U.S. Government has certain rights in the invention described, which was made in part with funds from the National Institutes of Health, Grant Number 1R01HD42011-01.

FIELD OF THE INVENTION

The present invention relates to the fields of embryology and molecular biology. More specifically, methods for the reproducible derivation of germ cells from stem cells are disclosed. Also provided are methods for obtaining transgenic stem cells from the germ cells of the invention and subjecting such cells to differentiation conditions to provide desired cell lineages for use in therapeutic cloning protocols. The invention also encompasses the reproducible production of oocytes from stem cells for use in reproductive cloning of non-human animals.

BACKGROUND OF THE INVENTION

Several publications and patent documents are cited throughout the specification in order to describe the state of the art to which this invention pertains. Each of these references is incorporated herein as though set forth in full.

Genetic modification of non-humans is useful for the production of genetically superior farm animals. Transgenic animals have been successfully produced via direct somatic cell nuclear transfer into a recipient enucleated oocyte which is then cultured under conditions conducive to blastocyst formation followed by transplantation of the resulting embryo into a surrogate animal. This methodology allows for the production of genetically identical individuals which have superior growth characteristics, e.g., greater milk production, leaner body mass, etc.

Therapeutic cloning methods for the repair of human tissues provides great promise for the treatment of human disease. To date, however such approaches have relied upon the use of human embryos which raises a variety of moral and ethical concerns. These concerns have hampered the progress of the research. It would be highly advantageous if compositions and methods were available for reproducibly generating germ cells from a continuous source of mammalian embryonic stem cells. If such germ cells could then be induced to form oocytes and spermatogonia, such methods would provide a powerful approach for the treatment of infertile couples. Oocytes so obtained could also be genetically transformed and induced to differentiate into desired cell types, for use in the generation of tissues for therapeutic cloning. Such methods would obviate the need for harvesting oocytes and would provide a continuous source for such cells. Additionally, the ethical concerns of harvesting human oocytes would be overcome by such a method.

SUMMARY OF THE INVENTION

In accordance with the present invention, compositions and methods for the reproducible derivation of germ cells from human stem cells are provided.

In one embodiment of the invention, a germ cell specific marker comprising a germ cell specific promoter sequence optionally operably linked to a reporter gene is provided. In a preferred embodiment the germ cell specific marker comprises a truncated Oct4 promoter gene sequence having the sequence of SEQ ID NO: 1.

In yet another embodiment of the invention, a method for deriving germ cells from embryonic stem cells is disclosed. An exemplary method comprises the following steps: i) transforming embryonic stem cells with a germ cell specific promoter sequence operably linked to a reporter gene; ii) culturing the transformed cells in ES cell medium under conditions which promote differentiation; iii) detaching the cultured cells; iv) replating the detached cells in medium which prevents further differentiation of the cells; v) monitoring the replated cells for reporter gene expression thereby identifying germ cells in a mixed cell population; and vi) isolating the germ cells identified from step v).

In preferred embodiments of the foregoing method, the cells are further subjected to culture conditions that promote the formation of oocytes or spermatogonia.

Germ cells, oocytes and spermatogonia obtained by the aforementioned method are also encompassed by the present invention.

In yet another embodiment of the invention, it has been discovered that the foregoing culture conditions may be utilized to derive germ cells from stem cells in the absence of the transgene described above. In this method, germ cells are derived from embryonic stem cells by i) culturing the stem cells in ES cell medium under conditions which promote differentiation; ii) detaching the cultured cells; iii) replating the detached cells in medium which prevents further differentiation of said cells; iv) monitoring the replated cells for morphological alterations associated with germ cell formation; and v) isolating the germ cells identified from the morphological alterations observed in step d). Cells isolated using the foregoing methods can be identified in culture via the appearance of morphological changes which comprise at least one of the following: cell enlargement, increased spherical appearance, and reduced cell to cell contacts.

Germ cells, oocytes and spermatogonia obtained by the aforementioned method which lack a transgene are also encompassed by the present invention.

In yet another aspect of the invention a method for deriving germ cells from embryoid bodies is provided. An exemplary method comprises: i) transforming embryonic stem cells with a germ cell specific marker comprising a truncated Oct4 gene promoter linked to a reporter gene; ii) culturing cells comprising the germ cell specific marker under conditions which promote the formation of embryoid bodies; iii) monitoring the cultured embryoid bodies for germ cell specific reporter gene expression; and iv) isolating germ cells from the cultured embryoid bodies. Germ cells, oocytes and spermatogonia obtained from embryoid culture are also encompassed by the present invention.

Also in accordance with the invention, are methods for preparing a non-human embryo which has the capacity to generate a live-born animal. An exemplary method comprises i) obtaining an oocyte as set forth in any of the methods above;

ii) transferring a somatic cell nucleus into said oocyte after enucleating the same to form a chimeric oocyte; and iii) culturing said chimeric oocyte under conditions which result in the establishment of a non-human embryo. This method may further comprise implanting the embryo into a recipient female so as to produce a fetus that undergoes full fetal development and parturition to generate said live born animal. Animals obtained via the foregoing method are also encompassed within the invention. In a further embodiment of the method to create a non-human animal, the method may optionally comprise the step of transforming the somatic cell nucleus with a corrective nucleic acid sequence prior to transferring said nucleus into said enucleated oocyte.

In yet another aspect of the invention, a method for generating genetically identical oocytes from an infertile female is disclosed. An exemplary method entails i) obtaining an oocyte as set forth in any of the foregoing methods; ii) transferring a somatic cell nucleus from said infertile female into the oocyte after enucleating the same to form a chimeric oocyte; iii) culturing the oocyte under conditions suitable to induce blastocyst formation; iv) isolating embryonic stem cells from the blastocyst; v) deriving germ cells from the stem cells; and vi) culturing the germ cells under conditions that promote the formation of oocytes, and vii) isolating the oocytes from step vi), the oocytes being genetically identical to the infertile female. Also encompassed by the invention are oocytes generated from this method.

In a further embodiment of the invention, a method for therapeutic cloning of tissues for the treatment of disease in a patient is disclosed. An exemplary method comprises: i) obtaining an oocyte as described above; ii) transferring a somatic cell nucleus from the patient into an oocyte after enucleating the same to form a chimeric oocyte; iii) culturing the oocyte under conditions suitable to induce blastocyst formation; iv) isolating embryonic stem cells from the blastocyst; v) exposing the cells to a receptor ligand cocktail which induces the stem cells to differentiate into a desired cell type; vi) culturing the cells of step v) for a suitable time period to generate an effective amount of cells of said desired cell type; and vii) optionally isolating the cells of step vi). The method for therapeutic cloning may optionally comprise introduction of a corrective nucleic acid sequence into the stem cells of step iv).

An alternative method for therapeutic cloning in a patient entails the following steps: i) obtaining an oocyte as set forth above; ii) transferring a somatic cell nucleus from the patient into the oocyte after enucleating the same to form a chimeric oocyte; iii) culturing the oocyte under conditions suitable to induce blastocyst formation; iv) isolating embryonic stem cells from the blastocyst; v) transforming the stem cells with a nucleic acid construct comprising a tissue specific molecule operably linked to a sequence encoding a selectable marker; vi) culturing the cells in the presence of selection agent, those cells comprising the construct surviving in the presence of said selection agent, thereby generating a culture of the desired cell type; vii) culturing the cells of step vi) for a suitable time period to generate an effective amount of cells of said desired cell type; and viii) optionally isolating the cells of step vii). This method may also comprise the optional transformation of the stem cells of step iv with a corrective nucleic acid sequence.

In a final aspect of the invention, a method for screening test compounds for toxicity or teratogenic potential is provided. An exemplary method comprises: i) providing an oocyte as described herein; ii) exposing the oocytes to increasing amounts of the test compound; and iii) culturing the oocytes under conditions that promote blastocyst formation; and iv) determining the effect, if any, of the test compound on the ability of said oocyte to form a blastocyst.

BRIEF DESCRIPTIONS OF THE DRAWING

Figure 1A:
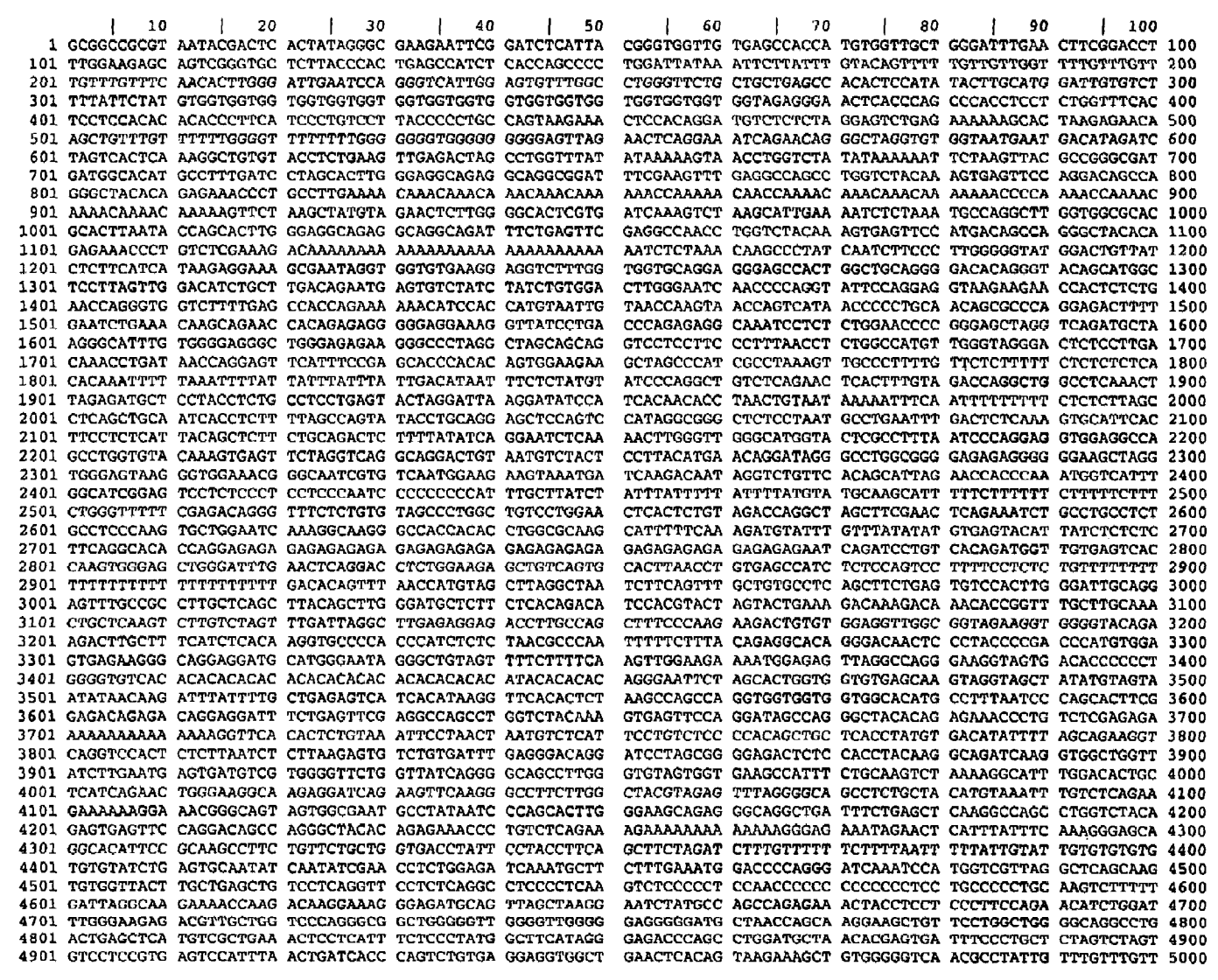
Figure 1B:
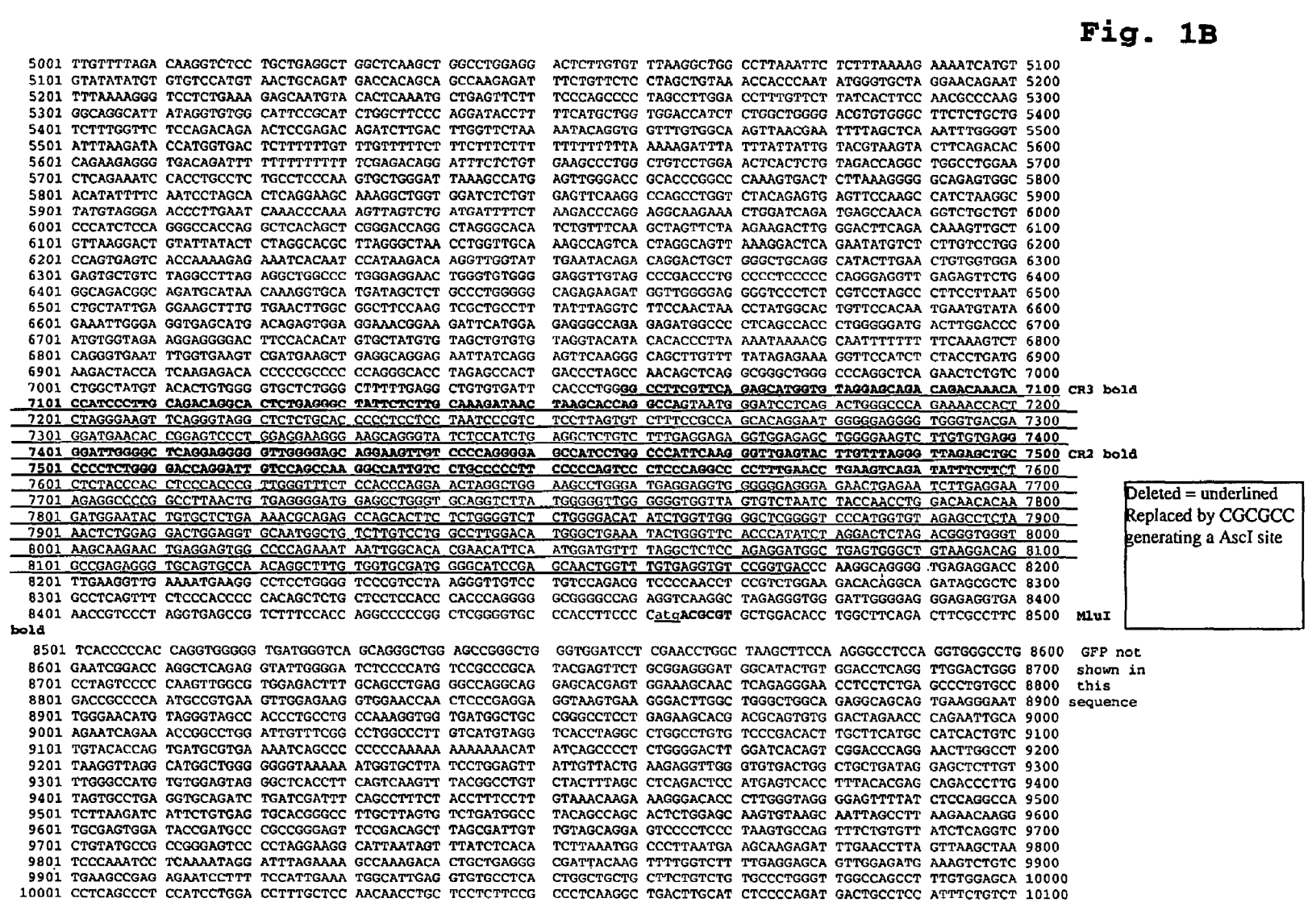
Figure 1C:
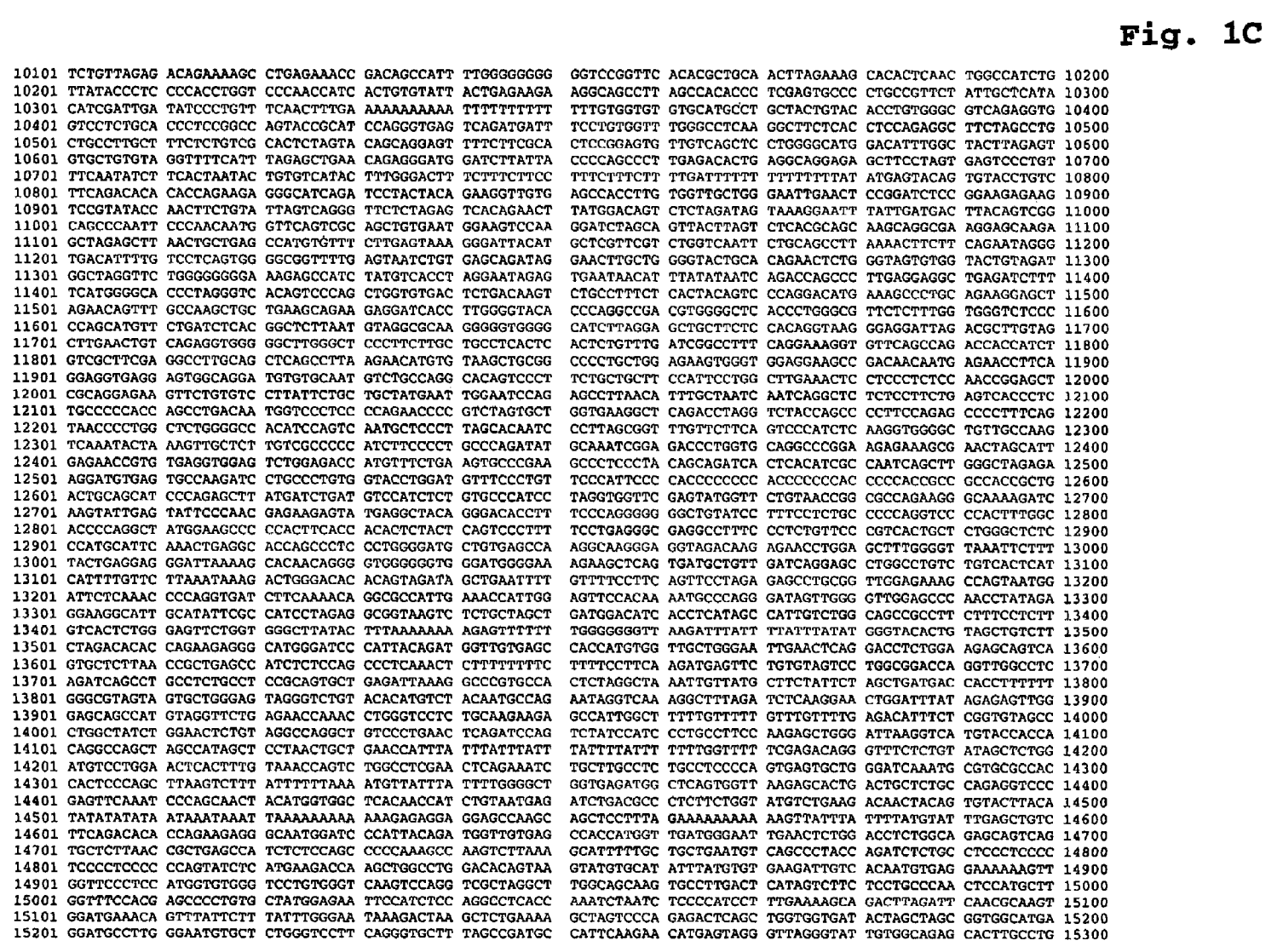

FIGS. 1A-1D provides the nucleic acid sequence for the GC-Oct4 transgene. The underlined portion of the sequence is deleted to gain germ line specific expression of the transgene (SEQ ID NO: 1).

Figure 2B:

FIGS. 2A and 2B are micrographs of oocyte cultures obtained via use of the truncated transgene (FIG. 2A) and in the absence of the transgene (FIG. 2B). As shown in the figures, oocytes can be identified morphologically and isolated in the absence of GFP following culturing of the cells as described herein.

DETAILED DESCRIPTION OF THE INVENTION

In accordance with the present invention, methods and compositions are provided for deriving germ cells from stem cells and embryoid bodies using a viable germ cell specific marker. In these methods, a germ cell specific marker comprising a truncated version of the Oct4 gene linked to a reporter gene, preferably green fluorescent protein (GFP), is used in methods for deriving germ cells from embryoid bodies and embryonic stem cells under conditions known to abolish pluripotency. Oocytes obtained using the germ cells of the invention can then be used in therapeutic and reproductive cloning protocols.

Stem cells can be derived from a number of different sources. These sources include early embryos (blastocysts) created by in vitro fertilization; early embryos created by inserting the nucleus from an adult cell into an egg with its nucleus removed; germ cells or organs of an aborted fetus; blood cells of the umbilical cord at the time of birth; certain adult tissues (e.g. bone marrow); and mature adult tissue cells which have been reprogrammed to behave like stem cells. Theoretically, stem cells taken from fetal tissue are the most pluripotent. Methods for reprogramming mature adult cells to "dedifferentiate" into stem cells are still in their infancy.

Tissues derived from stem cells have great potential for use in the treatment of a variety of disorders by replacing cells that have become damaged or diseased. Examples include, without limitation, the use of insulin secreting cells in diabetic patients, nerve cells in stroke or Parkinson's disease patients; or liver cells to repair a damaged organ.

The use of oocytes derived in accordance with the methods of the invention also enables females with mitochondrial DNA damage to successfully have offspring using a donor enucleated oocyte into which a somatic cell nucleus isolated from a cell from the female is introduced.

The germ cell specific marker described herein comprises a truncated Oct4 gene. The Oct4 gene encodes a transcription factor that is expressed in embryonic stem cells and germ cells of the mouse embryo. This gene has been demonstrated to be expressed in both the pluripotent founder population of the embryo as well as in the germ cell lineage (Pesce, M. and Schöler, H. R. Mol. Reprod. Dev. 2000 55:452-457). Expression of reporter genes LacZ and Green Fluorescent Protein inserted into an 18 kb genomic fragment encompassing the Oct4 gene has been shown to come close to mimicking the endogenous embryonic expression pattern in Oct4 transgenic mice (Yoshimuzu et al. Develop. Growth Differ. 1999 41:675-684; Yeom et al. Development 1996 122:881-894). Cells that differentiate into somatic tissue no longer express Oct4.

Orthologs to the murine Oct4 gene have been identified in a variety of species. The murine Oct4 gene is highly conserved in humans and cows, as evidenced by 87% and 81.7% overall protein sequence identity, genomic organization into 5 exons, and chromosomal mapping to the major histocompatibility complex (MHC; Takeda et al. 1992; Abdel-Rahman et al. 1995, van Eijk et al. 1999). The organization of the bovine Oct4 is similar to the human ortholog sharing 90.6% overall identity at the protein level and strong conservation of the gene structure and gene localization (van Eijk et al. 1999). A detailed sequence comparison of human, bovine and murine Oct4 is disclosed by Nordhoff et al. (Mammalian Genome 2001 12:309-317).

It has now been found that deleting two of the four regions of Oct4 conserved between humans, bovine and mouse (CR2 and 3) generated a transgene which is specifically expressed in germ cells. This germ cell specific transgene is referred to herein as GC-Oct4. The nucleic acid sequence for GC-Oct4 is depicted in FIG. 1. The underlined portion of the sequence is deleted in order to gain germ cell specific expression of the transgene. Inclusion of the underlined sequence results in expression in embryonic stem cells as well as germ cells thereby confounding efforts to isolate germ cells in a mixed cell population. In a preferred embodiment, this transgene is linked to a reporter gene such as GFP, for easy monitoring of expression of the transgene in germ cells. Use of a detectable label facilitates monitoring of the differentiation process of the germ cells and also facilitates isolation and further characterization thereof. The GFP label also allows viable cell sorting. The GFP fluorescence can be used in combination with antibodies, for example antibodies specific for the receptor c-kit to isolate and further characterize germ cells.

Importantly, male or female stem cells can be used as the starting stem cells in the instant invention of deriving and isolating germ cells.

In certain circumstances, once germ cells are isolated in accordance with the invention, it may be desirable to remove the transgene from the cells. This can be accomplished by employing the cre/lox system described in U.S. Pat. No. 5,919,676 "Adenoviral vector system comprising Cre-loxP recombination"; U.S. Pat. No. 6,171,861 "Recombinatorial cloning using engineered recombination sites"; U.S. Pat. No. 6,262,341 "Method for the integration of foreign DNA into eukaryotic genomes"; and U.S. Pat. No. 6,461,864 "Methods and vector constructs for making non-human animals which ubiquitously express a heterologous gene.

Once germ cells are successfully derived and isolated, they can be cultured under conditions that give rise to oocytes or sperm cells. Oocytes generated in accordance with the methods described herein may be used to advantage in methods for therapeutic cloning and reproductive cloning in mammals.

The following definitions are provided to facilitate an understanding of the present invention:

The term "autologous" implies identical nuclear genetic identity between donor cells or tissue and those of the recipient.

A "hybrid cell" refers to the cell immediately formed by the fusion of a unit of cytoplasm formed from the fragmentation of an oocyte or zygote with an intact somatic or stem cell or alternatively a derivative portion of said somatic or stem cell, containing the nucleus.

The term "karyoplast" refers to a fragment of a cell containing the chromosomes and nuclear DNA. A karyoplast is surrounded by a membrane, either the nuclear membrane or other natural or artificial membrane.

"Multipotent" implies that a cell is capable, through its progeny, of giving rise to several different cell types found in the adult animal.

"Pluripotent" implies that a cell is capable, through its progeny, of giving rise to all the cell types which comprise the adult animal including the germ cells. Both embryonic stem and embryonic germ cells are pluripotent cells under this definition.

A "reconstructed embryo" is an embryo made by the fusion of an enucleated oocyte with a somatic or ES or EG cell; alternatively, the somatic cell nucleus can be injected into the oocyte.

The term "transgenic" animal or cell refers to animals or cells whose genome has been subject to technical intervention including the addition, removal, or modification of genetic information. The term "chimeric" also refers to an animal or cell whose genome has modified.

A "zygote" refers to a fertilized one-cell embryo.

The term "totipotent" as used herein can refer to a cell that gives rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps. Totipotent cells may also be used to generate incomplete animals such as those useful for organ harvesting, e.g., having genetic modifications to eliminate growth of an organ or appendage by manipulation of a homeotic gene.

A "blastocyst" is a preimplantation embryo that develops from a morula. A blastocyst has an outer layer called the trophoblast that is required for implantation into the uterine epithelium and an inner cell mass that contains the embryonic stem cells and will give rise to the embryo proper. A blastocyst normally contains a blastocoel or a blastocoelic cavity.

The term "follicle" refers to a more or less spherical mass of cells usually containing a cavity. Ovarian follicles comprise egg cells and the corona radiata.

An "embryoid body" (EB) is a three dimensional structure that forms from differentiated embryonic stem cells. Cellular derivatives of all three germ layers have been generated from embryoid bodies, such as hematopoietic, endothelial, muscle and neuronal cells.

The term "live born" as used herein preferably refers to an animal that exists ex utero. A "live born" animal may be an animal that is alive for at least one second from the time it exits the maternal host. A "live born" animal may not require the circulatory system of an in utero environment for survival. A "live born" animal may be an ambulatory animal. Such animals can include pre- and post-pubertal animals. As discussed previously, a live born animal may lack a portion of what exists in a normal animal of its kind.

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (3.sup.rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; and Animal Cells: culture and media, 1994, D. C. Darling, S. J. Morgan John Wiley and Sons, Ltd.

The term "cell line" as used herein can refer to cultured cells that can be passaged at least one time without terminating. The invention relates to cell lines that can be passaged at least 1, 2, 5, 10, 15, 20, 30, 40, 50, 60, 80, 100, and 200 times. Cell passaging is defined hereafter.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel which has been supplemented with medium suitable for further cell proliferation.

The term "proliferation" as used herein in reference to cells can refer to a group of cells that can increase in number over a period of time.

The term "permanent" or "immortalized" as used herein in reference to cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells die in culture.

The term "alkaline phosphatase positive" as used herein can refer to a detectable presence of cellular alkaline phosphatase. Cells that are not alkaline phosphatase positive do not stain appreciably using a procedure for visualizing cellular alkaline phosphatase. Procedures for detecting the presence of cellular alkaline phosphatase are well-known to a person of ordinary skill in the art. See, e.g., Matsui et al., 1991, "Effect of Steel Factor and Leukemia Inhibitory Factor on Murine Primordial Germ Cells in Culture," Nature 353: 750-752. Examples of cells that stain appreciably for alkaline phosphatase can be found in the art. See, e.g., U.S. Pat. No. 5,453,357, Entitled "Pluripotent Embryonic Stem Cells and Methods of Making Same," issued to Hogan on Sep. 26, 1995.

The term "precursor cell" or "precursor cells" as used herein can refer to a cell or cells used to establish cultured mammalian cells or a cultured mammalian cell line. A precursor cell or cells may be isolated from nearly any cellular entity. For example, a precursor cell or cells may be isolated from blastocysts, embryos, fetuses, and cell lines (e.g., cell lines established from embryonic cells), preferably isolated from fetuses and/or cell lines established from fetal cells, and more preferably isolated from ex utero animals and/or cell cultures and/or cell lines established from such ex utero animals. An ex utero animal may exist as a newborn animal (e.g., 5 days after birth), adolescent animal (e.g., pre-pubescent animal), pubescent animal (e.g., after ovulation or production of viable sperm), and adult animal (e.g., post pubescent). The ex utero animals may be alive or post mortem. Precursor cells may be cultured or non-cultured. Furthermore, precursor cells may be at a time cryopreserved or frozen (e.g., cryopreserved cells may be utilized as precursor cells to establish a cell culture). These examples are not meant to be limiting.

The term "reprogramming" or "reprogrammed" as used herein can refer to materials and methods that can convert a cell into another cell having at least one differing characteristic. Also, such materials and methods may reprogram or convert a cell into another cell type that is not typically expressed during the life cycle of the former cell. For example, (1) a non-totipotent cell can be reprogrammed into a totipotent cell; (2) a precursor cell can be reprogrammed into a cell having a morphology of an EG cell; and (3) a precursor cell can be reprogrammed into a totipotent cell. An example of materials and methods for converting a precursor cell into a totipotent cell having EG cell morphology is described hereafter.

The phrase "embryonal carcinoma cells" refers to cancer cells that exhibit the properties of multipotent stem cells and have the capacity for differentiation into different cell lineages.

The term "isolated" as used herein can refer to a cell that is mechanically separated from another group of cells. Examples of a group of cells are a developing cell mass, a cell culture, a cell line, and an animal.

The term "non-embryonic cell" as used herein can refer to a cell that is not isolated from an embryo. Non-embryonic cells can be differentiated or nondifferentiated. Non-embryonic cells can refer to nearly any somatic cell, such as cells isolated from an ex utero animal. These examples are not meant to be limiting.

For the purposes of the present invention, the term "embryo" or "embryonic" as used herein can refer to a developing cell mass that has not implanted into an uterine membrane of a maternal host. Hence, the term "embryo" as used herein can refer to a fertilized oocyte, a pre-blastocyst stage developing cell mass, and/or any other developing cell mass that is at a stage of development prior to implantation into an uterine membrane of a maternal host. Embryos of the invention may not display a genital ridge. An "embryonic cell" is isolated from and/or has arisen from an embryo. An embryo can represent multiple stages of cell development. For example, a one cell embryo can be referred to as a zygote, a solid spherical mass of cells resulting from a cleaved embryo can be referred to as a morula, and an embryo having a blastocoel can be referred to as a blastocyst.

The term "fetus" as used herein can refer to a developing cell mass that has implanted into the uterine membrane of a maternal host. A fetus can include such defining features as a genital ridge, for example. A genital ridge is a feature easily identified by a person of ordinary skill in the art, and is a recognizable feature in fetuses of most animal species.

The term "fetal cell" as used herein can refer to any cell isolated from and/or has arisen from a fetus or derived from a fetus, including amniotic cells. The term "non-fetal cell" is a cell that is not derived or isolated from a fetus.

The term "parturition" as used herein can refer to a time that a fetus is delivered from female recipient. A fetus can be delivered from a female recipient by abortion, c-section, or birth.

The term "primordial germ cell" as used herein can refer to a diploid precursor cell capable of becoming a germ cell. Primordial germ cells can be isolated from any tissue in a developing cell mass, and are preferably isolated from genital ridge cells of a developing cell mass. A genital ridge is a section of a developing cell mass that is well-known to a person of ordinary skill in the art.

The term "embryonic stem cell" as used herein can refer to pluripotent cells isolated from an embryo that are maintained in in vitro cell culture. Such cells are rapidly dividing cultured cells isolated from cultured embryos which retain in culture the ability to give rise, in vivo, to all the cell types which comprise the adult animal, including the germ cells. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, Theriogenology 38: 315-335. See, e.g., Piedrahita et al., 1998, Biol. Reprod. 58: 1321-1329; Wianny et al., 1997, Biol. Reprod. 57: 756-764; Moore & Piedrahita, 1997, In Vitro Cell Biol. Anim. 33: 62-71; Moore, & Piedrahita, 1996, Mol. Reprod. Dev. 45: 139-144; Wheeler, 1994, Reprod. Fert. Dev. 6: 563-568; Hochereaude Reviers & Perreau, Reprod. Nutr. Dev. 33: 475-493; Strojek et al., 1990, Theriogenology 33: 901-903; Piedrahita et al., 1990, Theriogenology 34: 879-901; and Evans et al., 1990, Theriogenology 33: 125-129.

The term "differentiated cell" as used herein can refer to a precursor cell that has developed from an unspecialized phenotype to a specialized phenotype. For example, embryonic cells can differentiate into an epithelial cell lining the intestine. Materials and methods of the invention can reprogram differentiated cells into totipotent cells. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

The term "asynchronous population" as used herein can refer to cells that are not arrested at any one stage of the cell cycle. Many cells can progress through the cell cycle and do not arrest at any one stage, while some cells can become arrested at one stage of the cell cycle for a period of time. Some known stages of the cell cycle are G1, S, G2, and M. An asynchronous population of cells is not manipulated to synchronize into any one or predominantly into any one of these phases. Cells can be arrested in the M stage of the cell cycle, for example, by utilizing multiple techniques known in the art, such as by colcemid exposure. Examples of methods for arresting cells in one stage of a cell cycle are discussed in WO 97/07669, entitled "Quiescent Cell Populations for Nuclear Transfer".

The terms "synchronous population" and "synchronizing" as used herein can refer to a fraction of cells in a population that are within a same stage of the cell cycle. Preferably, about 50% of cells in a population of cells are arrested in one stage of the cell cycle, more preferably about 70% of cells in a population of cells are arrested in one stage of the cell cycle, and most preferably about 90% of cells in a population of cells are arrested in one stage of the cell cycle. Cell cycle stage can be distinguished by relative cell size as well as by a variety of cell markers well known to a person of ordinary skill in the art. For example, cells can be distinguished by such markers by using flow cytometry techniques well known to a person of ordinary skill in the art. Alternatively, cells can be distinguished by size utilizing techniques well known to a person of ordinary skill in the art, such as by the utilization of a light microscope and a micrometer, for example. In a preferred embodiment, cells are synchronized by arresting them (i.e., cells are not dividing) in a discreet stage of the cell cycle.

The terms "embryonic germ cell" and "EG cell" as used herein can refer to a cultured cell that has a distinct flattened morphology and can grow within monolayers in culture. An EG cell may be distinct from a fibroblast cell. This EG cell morphology is to be contrasted with cells that have a spherical morphology and form multicellular clumps on feeder layers. Embryonic germ cells may not require the presence of feeder layers or presence of growth factors in cell culture conditions. Additionally, germ cells may be derived from stem cells transformed with the Oct4 trangene as described more fully in the examples below.

The term "cumulus cell" as used herein can refer to any cultured or non-cultured cell that is isolated from cells and/or tissue surrounding an oocyte. Persons skilled in the art can readily identify a cumulus cell. Examples of methods for isolating and culturing cumulus cells are discussed in Damiani et al., 1996, Mol. Reprod. Dev. 45: 521-534; Long et al., 1994, J. Reprod. Fert. 102: 361-369; and Wakayama et al., 1998, Nature 394: 369-373.

The term "modified nuclear DNA" as used herein can refer to a nuclear deoxyribonucleic acid sequence of a cell, embryo, fetus, or animal of the invention that has been manipulated by one or more recombinant DNA techniques. Examples of recombinant DNA techniques are well known to a person of ordinary skill in the art, which can include (1) inserting a DNA sequence from another organism (e.g., a human organism) into target nuclear DNA, (2) deleting one or more DNA sequences from target nuclear DNA, and (3) introducing one or more base mutations (e.g., site-directed mutations) into target nuclear DNA. Cells with modified nuclear DNA can be referred to as "transgenic cells" or "chimeric cells" for the purposes of the invention. Transgenic cells can be useful as materials for nuclear transfer cloning techniques provided herein. The phrase "modified nuclear DNA" may also encompass "corrective nucleic acid sequence(s)" which replace a mutated nucleic acid molecule with a nucleic acid encoding a biologically active, phenotypically normal polypeptide. The constructs utilized to generate modified nuclear DNA may optionally comprise a reporter gene encoding a detectable product.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

"Selectable marker" as used herein refers to a molecule that when expressed in cells renders those cells resistant to a selection agent. Nucleic acids encoding selectable marker may also comprise such elements as promoters, enhancers, translational control sequences, polyA addition signals, transcriptional termination signals and the like. Suitable selection agents include antibiotic such as kanamycin, neomycin, and hygromycin.

Methods and tools for insertion, deletion, and mutation of nuclear DNA of mammalian cells are well-known to a person of ordinary skill in the art. See, Molecular Cloning, a Laboratory Manual, 2nd Ed., 1989, Sambrook, Fritsch, and Maniatis, Cold Spring Harbor Laboratory Press; U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos"; WO 98/16630, Piedrahita & Bazer, published Apr. 23, 1998, "Methods for the Generation of Primordial Germ Cells and Transgenic Animal Species. These methods include techniques for transfecting cells with foreign DNA fragments and the proper design of the foreign DNA fragments such that they effect insertion, deletion, and/or mutation of the target DNA genome.

Any of the cell types defined herein can be altered to harbor modified nuclear DNA. For example, embryonic stem cells, embryonic germ cells, fetal cells, and any totipotent cell defined herein can be altered to harbor modified nuclear DNA.

Examples of methods for modifying a target DNA genome by insertion, deletion, and/or mutation are retroviral insertion, artificial chromosome techniques, gene insertion, random insertion with tissue specific promoters, homologous recombination, gene targeting, transposable elements, and/or any other method for introducing foreign DNA. Other modification techniques well known to a person of ordinary skill in the art include deleting DNA sequences from a genome, and/or altering nuclear DNA sequences. Examples of techniques for altering nuclear DNA sequences are site-directed mutagenesis and polymerase chain reaction procedures. Therefore, the invention relates in part to mammalian cells that are simultaneously totipotent and transgenic. Such transgenic and totipotent cells can serve as nearly unlimited sources of donor cells for production of cloned transgenic animals.

The term "recombinant product" as used herein can refer to the product produced from a DNA sequence that comprises at least a portion of the modified nuclear DNA. This product can be a peptide, a polypeptide, a protein, an enzyme, an antibody, an antibody fragment, a polypeptide that binds to a regulatory element (a term described hereafter), a structural protein, an RNA molecule, and/or a ribozyme, for example. These products are well defined in the art.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art. In a preferred embodiment, the promoters of the invention drive germ line specific expression of the transgenes described herein. Such promoters include the truncated Oct4 promoter, the GCNA promoter, the c-kit promoter and the mouse Vasa-homologue protein (mvh) promoter.

The term "enhancers" or "enhancer" as used herein can refer to a DNA sequence that is located adjacent to the DNA sequence that encodes a recombinant product. Enhancer elements are typically located upstream of a promoter element or can be located downstream of a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The term "nuclear transfer" as used herein can refer to introducing a full complement of nuclear DNA from one cell to an enucleated cell. Nuclear transfer methods are well known to a person of ordinary skill in the art. See, e.g., Nagashima et al., 1997, Mol. Reprod. Dev. 48: 339-343; Nagashima et al., 1992, J. Reprod. Dev. 38: 73-78; Prather et al., 1989, Biol. Reprod. 41: 414-419; Prather et al., 1990, Exp. Zool. 255: 355-358; Saito et al., 1992, Assis. Reprod. Tech. Andro. 259: 257-266; and Terlouw et al., 1992, Theriogenology 37: 309. Nuclear transfer may be accomplished by using oocytes that are not surrounded by a zona pellucida.

The term "cryopreserving" as used herein can refer to freezing a cell, embryo, or animal of the invention. Cells, embryos, or portions of animals of the invention are frozen at temperatures preferably lower than 0° C., more preferably lower than −80° C., and most preferably at temperatures lower than −196° C. Cells and embryos of the invention can be cryopreserved for an indefinite amount of time. It is known that biological materials can be cryopreserved for more than fifty years and still remain viable. For example, bovine semen that is cryopreserved for more than fifty years can be utilized to artificially inseminate a female bovine animal and result in the birth of a live offspring. Methods and tools for cryopreservation are well-known to those skilled in the art. See, e.g., U.S. Pat. No. 5,160,312, entitled "Cryopreservation Process for Direct Transfer of Embryos," issued to Voelkel on Nov. 3, 1992.

The term "thawing" as used herein can refer to a process of increasing the temperature of a cryopreserved cell, embryo, or portions of animals. Methods of thawing cryopreserved materials such that they are active after a thawing process are well-known to those of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

The term "antibiotic" as used herein can refer to any molecule that decreases growth rates of a bacterium, yeast, fungi, mold, or other contaminants in a cell culture. Antibiotics are optional components of cell culture media. Examples of antibiotics are well known in the art. See, Sigma and DIFCO catalogs.

The term "feeder cells" as used herein can refer to cells that are maintained in culture and are co-cultured with target cells. Target cells can be precursor cells, embryonic stem cells, embryonic germ cells, cultured cells, and totipotent cells, for example. Feeder cells can provide, for example, peptides, polypeptides, electrical signals, organic molecules (e.g., steroids), nucleic acid molecules, growth factors (e.g., bFGF), other factors (e.g., cytokines such as LIF and steel factor), and metabolic nutrients to target cells. Certain cells, such as embryonic germ cells, cultured cells, and totipotent cells may not require feeder cells for healthy growth. Feeder cells preferably grow in a mono-layer.

Feeder cells can be established from multiple cell types. Examples of these cell types are fetal cells, mouse cells, Buffalo rat liver cells, and oviductal cells. These examples are not meant to be limiting. Tissue samples can be broken down to establish a feeder cell line by methods well known in the art (e.g., by using a blender). Feeder cells may originate from the same or different animal species as precursor cells. Feeder cells can be established from ungulate fetal cells, mammalian fetal cells, and murine fetal cells. One or more cell types can be removed from a fetus (e.g., primordial germs cells, cells in the head region, and cells in the body cavity region) and a feeder layer can be established from those cells that have been removed or cells in the remaining dismembered fetus. When an entire fetus is utilized to establish fetal feeder cells, feeder cells (e.g., fibroblast cells) and precursor cells (e.g., primordial germ cells) can arise from the same source (e.g., one fetus).

The term "receptor ligand cocktail" as used herein can refer to a mixture of one or more receptor ligands. A receptor ligand can refer to any molecule that binds to a receptor protein located on the outside or the inside of a cell. Receptor ligands can be selected from molecules of the cytokine family of ligands, neurotrophin family of ligands, growth factor family of ligands, and mitogen family of ligands, all of which are well known to a person of ordinary skill in the art. Examples of receptor/ligand pairs are: epidermal growth factor receptor/epidermal growth factor, insulin receptor/insulin, cAMP-dependent protein kinase/cAMP, growth hormone receptor/growth hormone, and steroid receptor/steroid. It has been shown that certain receptors exhibit cross-reactivity. For example, heterologous receptors, such as insulin-like growth factor receptor 1 (IGFR1) and insulin-like growth factor receptor 2 (IGFR2) can both bind IGF1. When a receptor ligand cocktail comprises a stimulus, the receptor ligand cocktail can be introduced to a precursor cell in a variety of manners known to a person of ordinary skill in the art.

The term "cytokine" as used herein can refer to a large family of receptor ligands well-known to a person of ordinary skill in the art. The cytokine family of receptor ligands includes such members as leukemia inhibitor factor (LIF); cardiotrophin 1 (CT-1); ciliary neurotrophic factor (CNTF); stem cell factor (SCF), which is also known as Steel factor; oncostatin M (OSM); and any member of the interleukin (IL) family, including IL-6, IL-1, and IL-12. The teachings of the invention do not require the mechanical addition of steel factor (also known as stem cell factor in the art) for the conversion of precursor cells into totipotent cells.

The term "cloned" as used herein can refer to a cell, embryonic cell, fetal cell, and/or animal cell having a nuclear DNA sequence that is substantially similar or identical to a nuclear DNA sequence of another cell, embryonic cell, fetal cell, and/or animal cell. A cloned embryo can arise from one nuclear transfer process, or alternatively, a cloned embryo can arise from a cloning process that includes at least one re-cloning step. If a cloned embryo arises from a cloning procedure that includes at least one re-cloning step, then the cloned embryo can indirectly arise from a totipotent cell since the re-cloning step can utilize embryonic cells isolated from an embryo that arose from a totipotent cell.

The term "implanting" as used herein in reference to embryos can refer to impregnating a female animal with an embryo described herein. Implanting techniques are well known to a person of ordinary skill in the art. See, e.g., Polge & Day, 1982, "Embryo transplantation and preservation," Control of Pig Reproduction, DJA Cole and GR Foxcroft, eds., London, UK, Butterworths, pp. 227-291; Gordon, 1997, "Embryo transfer and associated techniques in pigs," Controlled reproduction in pigs (Gordon, ed), CAB International, Wallingford UK, pp 164-182; and Kojima, 1998, "Embryo transfer," Manual of pig embryo transfer Procedures, National Livestock Breeding Center, Japanese Society for Development of Swine Technology, pp 76-79. The embryo may be allowed to develop in utero, or alternatively, the fetus may be removed from the uterine environment before parturition.

The term "nuclear donor" as used herein can refer to a cell or a nucleus from a cell that is translocated into a nuclear acceptor. A nuclear donor may be a totipotent mammalian cell. In addition, a nuclear donor may be any cell described herein, including, but not limited to a non-embryonic cell, a non-fetal cell, a differentiated cell, a somatic cell, an embryonic cell, a fetal cell, an embryonic stem cell, a primordial germ cell, a genital ridge cell, a cumulus cell, an amniotic cell, a fetal fibroblast cell, a hepatacyte, an embryonic germ cell, an adult cell, a cell isolated from an asynchronous population of cells, and a cell isolated from a synchronized population of cells where the synchronous population is not arrested in the G0 stage of the cell cycle. A nuclear donor cell can also be a cell that has differentiated from an embryonic stem cell. See, e.g., Piedrahita et al., 1998, Biol. Reprod 58: 1321-1329; Shim et al., 1997, Biol. Reprod. 57: 1089-1095; Tsung et al., 1995, Shih Yen Sheng Wu Hsuch Pao 28: 173-189; and Wheeler, 1994, Reprod Fertil. Dev. 6: 563-568. In addition, a nuclear donor may be a cell that was previously frozen or cryopreserved.

The term "enucleated oocyte" as used herein can refer to an oocyte which has had its nucleus or its chromosomes removed. Typically, a needle can be placed into an oocyte and the nucleus can be aspirated into the needle. The needle can be removed from the oocyte without rupturing the plasma membrane. This enucleation technique is well known to a person of ordinary skill in the art. See, U.S. Pat. No. 4,994,384; U.S. Pat. No. 5,057,420; and Willadsen, 1986, Nature 320:63-65. An enucleated oocyte is preferably prepared from an oocyte that has been matured for greater than 24 hours, preferably matured for greater than 36 hours, more preferably matured for greater than 48 hours, and most preferably matured for about 53 hours.

The terms "maturation" and "matured" as used herein can refer to a process in which an oocyte is incubated in a medium in vitro. Maturation media can contain multiple types of components, including hormones and growth factors. Time of maturation can be determined from the time that an oocyte is placed in a maturation medium to the time that the oocyte is subject to a manipulation (e.g., enucleation, nuclear transfer, fusion, and/or activation). Oocytes can be matured in multiple media well known to a person of ordinary skill in the art. See, e.g., Mattioli et al., 1989, Theriogenology 31: 1201-1207; Jolliff & Prather, 1997, Biol. Reprod. 56: 544-548; Funahashi & Day, 1993, J. Reprod. Fert. 98: 179-185; Nagashima et al., 1997, Mol. Reprod. Dev. 38: 339-343; Abeydeera et al., 1998, Biol. Reprod. 58: 213-218; Funahashi et al., 1997, Biol. Reprod. 57: 49-53; and Sawai et al., 1997, Biol. Reprod. 57: 1-6. Oocytes can be matured for any period of time: an oocyte can be matured for greater than 10 hours, greater than 20 hours, greater than 24 hours, greater than 60 hours, greater than 72 hours, greater than 90 hours, preferably matured for greater than 36 hours, more preferably matured for greater than 48 hours, and most preferably matured for about 53 hours. The term "about" with respect to oocyte maturation can refer to plus or minus 3 hours.

The term "injection" as used herein in reference to embryos, can refer to perforation of an oocyte with a needle, and insertion of a nuclear donor in the needle into the oocyte. In preferred embodiments, a nuclear donor may be injected into the cytoplasm of an oocyte or in the perivitelline space of an oocyte. This direct injection approach is well known to a person of ordinary skill in the art, as indicated by publications already incorporated herein in reference to nuclear transfer. For a direct injection approach to nuclear transfer, a whole cell may be injected into an oocyte, or alternatively, a nucleus isolated from a cell may be injected into an oocyte. Such an isolated nucleus may be surrounded by nuclear membrane only, or the isolated nucleus may be surrounded by nuclear membrane and plasma membrane in any proportion. An oocyte may be pre-treated to enhance the strength of its plasma membrane, such as by incubating the oocyte in sucrose prior to injection of a nuclear donor.

The term "electrical pulses" as used herein can refer to subjecting a nuclear donor and recipient oocyte to electric current. For nuclear transfer, a nuclear donor and recipient oocyte can be aligned between electrodes and subjected to electrical current. Electrical current can be alternating current or direct current. Electrical current can be delivered to cells for a variety of different times as one pulse or as multiple pulses. Cells are typically cultured in a suitable medium for delivery of electrical pulses. Examples of electrical pulse conditions utilized for nuclear transfer are well known in the art.

The term "fusion agent" as used herein can refer to any compound or biological organism that can increase the probability that portions of plasma membranes from different cells will fuse when a nuclear donor is placed adjacent to a recipient oocyte. In preferred embodiments fusion agents are selected from the group consisting of polyethylene glycol (PEG), trypsin, dimethylsulfoxide (DMSO), lectins, agglutinin, viruses, and Sendai virus. These examples are not meant to be limiting and other fusion agents known in the art are applicable and included herein.

The term "activation" can refer to any materials and methods useful for stimulating a cell to divide before, during, and after a nuclear transfer step. The term "cell" as used in the previous sentence can refer to an oocyte, a nuclear donor, and an early stage embryo. These types of cells may require stimulation in order to divide after nuclear transfer has occurred. The invention pertains to any activation materials and methods known to a person of ordinary skill in the art.

Examples of components that are useful for non-electrical activation include ethanol; inositol trisphosphate ($IP_3$); divalent ions (e.g., addition of $Ca^{2+}$ and/or $Sr^{2+}$); microtubule inhibitors (e.g., cytochalasin B); ionophores for divalent ions (e.g., the $a^{3+}$ ionophore ionomycin); protein kinase inhibitors (e.g., 6-dimethylaminopurine (DMAP)); protein synthesis inhibitors (e.g., cyclohexamide); phorbol esters such as phorbol 12-myristate 13-acetate (PMA); and thapsigargin. It is also known that temperature change and mechanical techniques are also useful for non-electrical activation. The invention includes any activation techniques known in the art. See, e.g., U.S. Pat. No. 5,496,720, entitled "Parthenogenic Oocyte Activation," issued on Mar. 5, 1996, Susko-Parrish et al., and Wakayama et al., 1998, Nature 394: 369-374.

When ionomycin and DMAP are utilized for non-electrical activation, ionomycin and DMAP may be introduced to cells simultaneously or in a step-wise addition, the latter being a preferred mode.

The term "inner cell mass" as used herein can refer to cells that give rise to the embryo proper. Cells that line the outside of a blastocyst can be referred to as a trophoblast of the embryo. Methods for isolating inner cell mass cells from an embryo are well known to a person of ordinary skill in the art, as discussed previously. The term "pre-blastocyst" is well known in the art and is referred to previously.

In one embodiment of the invention germ cells are derived from embryoid bodies (EB) of ES cells stably transformed with the GC-Oct4-GFP transgene described herein. To derive the germ cells, GC-Oct4 ES cell cultures are depleted of all MEF cells and cultured as EBs. See Example 3 herein. Germs cells derived from EBs via this method expressed GFP as measured by fluorescence. EBs after 5 days exhibited only weak GFP expression. After 15 days, GFP expression increased, with various regions of the EBs containing several layers of fluorescent cells. After day 23 EBs showed high levels of GFP. Typically, GFP-expressing cells formed a ring and covered about 50% of the EBs. However, GFP-positive cells can also be located in a single area. Germ cells derived from EBs via this method also expressed the germ-cell marker GCNA1. Typically between day 5 to 15, GCNA1 staining was detected in EBs sectioned and immunostained with GCNA1 antibodies and a peroxidase labeled avidin-biotin detection system using diaminobenzidine (DAB) as substrate. GCNA1-positive cells stain brown. These GFP-positive cells can be flow-sorted and more than 80% of the GFP positive cells are c-kit positive. The presence of these markers indicate that these cells correspond to early germ cells.

In addition to the generation of early germ cells, the GC-Oct4 ES cell cultures can also be differentiated into oocytes. See Examples 4 to 6. Observation of the outgrowing EBs described in Example 4 over a 16 week period revealed formation of confined longitudinal structures (CLS) in about three week old cultures. GFP-positive cells (germ cells) formed throughout the cultures but at that stage were not restricted to any particular area. CLS formation increased steadily for an additional 2 weeks. GFP-positive germ cells could then be detected mainly within these CLS. Thereafter, GFP-negative cells did not further proliferate, while GFP-positive cell proliferation increased outside the CLS, followed by new CLS formation and a subsequent decrease in germ cell proliferation. A repetition of this "cycle" took place about every 30 to 40 days and was observed over the entire 16 weeks of the experiment. The first onset of CLS formation coincided with the detection of a small population of both GFP expressing and non-expressing cells, which morphologically resembled oocytes. Over the time course an increase in number and morphological changes within that cell population were observed.

Germ cells derived directly from adherent ES cells (see Example 5) show onset of GFP expression at around day 3-4 with about 30% of all cells being fluorescent on day 6-7. Further cultivation revealed formation of follicular structures at around day 8-12 and a small number of oocyte cells about 3 weeks later (see Example 5). Thereafter, the cultures cycled as described in the previous paragraph, with the first CLS being detected in cultures at about 5-weeks.

GFP fluorescence was observed in germ cells derived directly from ES cells (see Example 5) and was detected first around 3.2 to 4 days later when "nebular-like" cell patches of GFP-positive germ cells were found. These cells always grew on another layer of cells that formed within the same culture of GC-Oct4 ES cells. Some of these cell patches underwent morphological changes upon further differentiation. Cells increased in size and spread apart from each other. Seven to ten days after initiation of differentiation these larger cells loosened off the plate and formed small aggregates with a very weak GFP signal (see example 6). The decrease in GFP signal reflexts down regulation of Oct-4. In developing germ cells in vivo, Oct-4 is down-regulated when mouse vasa homologue protein (mvh) is upregulated. When subjected to immunocytochemistry using an antibody specific for mvh these aggregates stained positive for mvh. Once replated in ES media lacking LIF these cells formed follicular structures and produced a substantial number of oocytes within the next 2-3 weeks.

To confirm that these structures were indeed oocytes, they were subjected to immunocytochemistry using antibodies immunospecific for zona pellucida 3 (ZP3). As expected, the structures stained positive for ZP3. The ability to obtain oocytes from continuous lines of stem cells as described above, facilitates methods for therapeutic cloning and reproductive cloning of non-human animals.

Uses of the Oocytes of the Invention in Methods for Therapeutic Cloning

The ability to obtain oocytes from stem cells provides the means to reproducibly generate replacement cells or tissues which are useful in therapeutic cloning protocols. In such protocols, a stem cell population is provided which is transformed with the GC-Oct4 transgene of the invention. These cells are cultured and germ cells are derived as described above. The germ cells are further cultured to generate oocyte structures. Once oocytes are obtained, they may be enucleated as set forth above. Somatic cell nuclei are obtained from the patient to be treated and somatic cell transfer is then performed. If the patient to be treated has a genetic mutation that is undesirable, the somatic cells utilized for nuclear transfer may optionally be transformed with a "corrective nucleic acid sequence" which corrects underlying genetic defect. These cells are then further cultured to form blastocysts from which transgenic stem cells may then be isolated. Transgenic stem cells so obtained may also be optionally transfected at this point with a "corrective nucleic acid sequence". The stem cells so obtained are then passaged and exposed to a receptor ligand cocktail to induce differentiation into the desired cell lineage as exemplified hereinbelow.

Tissues currently being developed from stem cells include, but are not limited to: blood vessels (Kocher, A. A. et al., Nature Med. (2001) 7:430-436; Jackson, K. A. et al., J. Clin. Invest. (2001) 107:1395-1402), bone (Petite, H. et al., Nature Biotech. (2000) 18:959-963), cartilage (Johnstone, B. et al., Clin. Orthop. (1999) S156-S162), cornea (Tsai, R. J. et al., N. Eng. J. Med. (2000) 343:86-93), dentin (Gronthos, S. et al., Proc. Natl. Acad. Sci. USA (2000) 97:13625-13620), heart muscle (Klug, M. G. et al., J. Clin. Invest. (1996) 98:216-224; review Boheler, K. R. et al., Cir. Res. (2002) 91:189-201), liver (Lagasse, E. et al., Nature Med. (2000) 6:1229-1234), pancreas (Soria, B. et al., Diabetes (2000) 49:1-6; Ramiya, V. K. et al., Nature Med. (2000) 6:278-282), nervous tissue (Bjorkland, A., Novaritis Found. Symp. (2000) 231:7-15; Lee, S. H. et al., Nature Biotechnology, (2000) 18:675-679; Kim, J. H. et al., Nature (2002) 418:50-56), skeletal muscle (Gussoni, E. et al., Nature (1999) 401:390-394), and skin (Pellegrini, G. et al., Transplantation (1999) 68:868-879). Some of the tissues being generated from stem cells are described in further detail below.

Neuronal Cells

Parkinson's disease is caused by the loss of midbrain neurons that synthesize the neurotransmitter dopamine. Delivery of dopamine-synthesizing neurons to the midbrain should alleviate the symptoms of the disease by restoring dopamine production. Stem cells obtained using the methods of the invention may be differentiated into dopamine-synthesizing neurons utilizing the protocols set forth below. (Lee, S. H. et al., Nature Biotechnology, (2000) 18:675-679; Kim, J. H. et al., Nature (2002) 418:50-56).

In a murine model, mouse ES cells were first transfected by electroporation with a plasmid expressing nuclear receptor related-1 (Nurr1), a transcription factor that has a role in the differentiation of midbrain precursors into dopamine neurons and a plasmid encoding neomycin resistance. Transfected clones (Nurr1 ES cells) were then subsequently isolated by culturing the cells in G418. The Nurr1 ES cells were then expanded under cultures which prevented differentiation (e.g., growth on gelatin-coated tissue culture plates in the presence of 1,400 U/ml-I of leukemia inhibitory factor (LIF; GIBCO/BRL, Grand Island, N.Y.) in ES cell medium consisting of knockout Dulbecco's minimal essential medium (GIBCO/BRL) supplemented with 15% FCS, 100 mM MEM nonessential amino acids, 0.55 mM 2-mercaptoethanol, L-glutamine, and antibiotics (all from GIBCO/BRL)). To induce EB formation, the cells were dissociated into a single-cell suspension by 0.05% trypsin and 0.04% EDTA in PBS and plated onto nonadherent bacterial culture dishes at a density of $2\text{-}2.5 \times 10^4$ cells/cm$^2$ in the medium described above. The EBs were formed for four days and then plated onto adhesive tissue culture surface in the ES cell medium. After 24 hours of culture, selection of nestin-positive cells, a marker of developmental neuorns, was initiated by replacing the ES cell medium by serum-free Dulbecco's modified Eagle's medium (DMEM)/F12 (1:1) supplemented with insulin (5 μg/ml), transferrin (50 μg/ml), selenium chloride (30 nM), and fibronectin (5 μg/ml) (ITSFn) medium. After 6-10 days of selection, expansion of nestin-positive cells was initiated. Specifically, the cells were dissociated by 0.05% trypsin/0.04% EDTA, and plated on tissue culture plastic or glass coverslips at a concentration of $1.5\text{-}2 \times 10^5$ cells/cm$^2$ in N2 medium modified (described in Johe, K. et al., Genes Dev. (1996) 10:3129-3140), and supplemented with 1 μg/ml of laminin and 10 ng/ml of bFGF (R&D Systems, Minneapolis, Minn.) in the presence of murine N-terminal fragment of sonic hedgehog (SHH; 500 ng/ml) and murine fibroblast growth factor (FGF) 8 isoform b (100 ng/ml; both from R&D Systems). Before cell plating, dishes and coverslips were precoated with polyornithine (15 mg/ml) and laminin (1 μg/ml, both from Becton Dickinson Labware, Bedford, Mass.). Nestin-positive cells were again expanded for six days. The medium was changed every two days. Differentiation was induced by removal of basic FGF (bFGF). The differentiation medium consisted of N2 medium supplemented with laminin (1 mg/ml) in the presence of cAMP (1 μM) and ascorbic acid (200 μM, both from Sigma, St. Louis, Mo.). The cells were incubated under differentiation conditions for 6-15 days.

78% of Nurr1 ES cells were found to be induced into dopamine-synthesizing, tyrosine hydroxylase (TH, a rate limiting enzyme in the biosynthesis of dopamine) positive neurons by the method set forth above. The resultant neurons were further characterized to express a variety of midbrain-specific markers such as Ptx3 and Engrailed 1 (En-1). The dopamine-synthesizing, TH$^+$ cells were also grafted into a rodent model of Parkinson's disease and were shown to extend axons, form functional synaptic connections, perform electrophysiological functions expected of neurons, innervate the striatum, and improve motor asymmetry.

Heart Muscle

The loss of cardiomyocytes from adult mammalian hearts is irreversible and leads to diminished heart function. Methods have been developed in which ES cells are employed as a renewable source of donor cardiomyocytes for cardiac engraftment (Klug, M. G. et al., J. Clin. Invest. (1996) 98:216-224).

ES cells were first transfected by electroporation with a plasmid expressing the neomycin resistance gene from an α-cardiac myosin heavy chain promoter and expressing the hygromycin resistance gene under the control of the phosphoglycerate kinase (pGK) promoter. Transfected clones were selected by growth in the presence of hygromycin (200 µg/ml; Calbiochem-Novabiochem). Transfected ES cells were maintained in the undifferentiated state by culturing in high glucose DMEM containing 10% fetal bovine serum (FBS), 1% nonessential amino acids, and 0.1 mM 2-mercaptoethanol. The medium was supplemented to a final concentration of 100 U/ml with conditioned medium containing recombinant LIF.

To induce differentiation, $2\times10^6$ freshly dissociated transfected ES cells were plated onto a 100-mm bacterial Petri dish containing 10 ml of DMEM lacking supplemental LIF. After 3 days in suspension culture, the resulting EBs were plated onto plastic 100-mm cell culture dishes and allowed to attach. Regions of cardiogenesis were readily identified by the presence of spontaneous contractile activity. For cardiomyocyte selection, the differentiated cultures were grown for 8 days in the presence of G418 (200 µg/ml; GIBCO/BRL). Cultures of selected ES-derived cardiomyocytes were digested with trypsin and the resulting single cell preparation was washed three times with DMEM and directly injected into the ventricular myocardium of adult mice.

The culture obtained by this method after G418 selection is more 99% pure for cardiomyocytes based on immunofluorescence for myosin. The obtained cardiomyocytes contained well defined myofibers and intercalated discs were observed to couple juxtaposed cells consistent with the observation that adjacent cells exhibit synchronous contractile activity. Importantly, the selected cardiomyocytes were capable of forming stable intercardiac grafts with the engrafted cells aligned and tightly juxtaposed with host cardiomyocytes.

Insulin-Producing Cells

An ideal treatment for diabetes is the restoration of β-cell function or mimicking the insulin secretory pattern of these cells. Insulin-secreting cells derived from ES cells have been generated by the following method and have been shown to be capable of normalizing blood glucose levels in a diabetic mouse model (Soria, B. et al., Diabetes (2000) 49:1-6).

ES cells were transfected by electroporation with a plasmid expressing β-gal under the control of the human insulin regulatory region and expressing the hygromycin resistance gene under the control of the pGK promoter. Transfected clones were selected by growth in the presence of hygromycin (200 µg/ml; Calbiochem-Novabiochem). Transfected ES cells were maintained in the undifferentiated state by culturing in high glucose Dulbecco's modified Eagle's medium (DMEM) containing 10% fetal bovine serum (FBS), 1% nonessential amino acids, 0.1 mM 2-mercaptoethanol, 1 mM sodium pyruvate, 100 IU/ml penicillin, and 0.1 mg/ml streptomycin. The medium was supplemented to a final concentration of 100 U/ml with conditioned medium containing recombinant LIF.

To induce differentiation to an insulin-secreting cell line, $2\times10^6$ hygromycin-resistant ES cells were plated onto a 100-mm bacterial Petri dish and cultured in DMEM lacking supplemental LIF. After 8-10 days in suspension culture, the resulting EBs were plated onto plastic 100-mm cell culture dishes and allowed to attach for 5-8 days. For ES Ins/β-gal selection, the differentiated cultures were grown in the same medium in the presence of 200 µg/ml G418. For final differentiation and maturation, the resulting clones were trypsinized and plated on a 100-mm bacterial Petri dish and grown for 14 days in DMEM supplemented with 200 µg/ml G418 and 10 mM nicotinamide (Sigma), a form of Vitamin B3 that may preserve and improve beta cell function. Finally, the resulting clusters were cultured for 5 days in RPMI 1640 media supplemented with 10% FBS, 10 mM nicotinamide, 200 µg/ml G418, 100 IU/ml penicillin, 0.1 mg/ml streptomycin, and low glucose (5.6 mM).

For cell implantation, ES-derived insulin-secreting cells were washed and resuspended in RPMI 1640 media supplemented with 10% FBS, 10 mM nicotinamide, 100 IU/ml penicillin, 0.1 mg/ml streptomycin, and 5.6 mM glucose at $5\times10^6$ cells/ml. The mice to receive the implantation of ES-derived insulin-secreting cells were male Swiss albino mice that had diabetic conditions induced by a single intraperitoneal injection of streptozotocin (STZ, Sigma) at 200 mg/kg body weight in citrate buffer. $1\times10^6$ cells were injected into the spleen of mice under anesthesia.

The ES-derived insulin-secreting cells produced from this method produced a similar profile of insulin production in response to increasing levels of glucose to that observed in mouse pancreatic islets. Significantly, implantation of the ES-derived insulin-secreting cells led to the correction of the hyperglycemia within the diabetic mouse, minimized the weight loss experienced by the mice injected with STZ, and lowered glucose levels after meal challenges and glucose challenges better than untreated diabetic mice and similar to control nondiabetic mice.

Human ES Cells

While the preceding examples describe the manipulation of murine ES cells, the current invention also encompasses the manipulation of human ES cells and the use of the same in the therapeutic cloning protocols described above. The technology for manipulating human ES cells is quite similar to the manipulation of murine ES cells, as the following example demonstrates (Schuldiner, M. et al., Proc. Natl. Acad. Sci. USA (2000) 97:11307-11312). Also see US Patent application 2002/0146,678.

Human ES cells, which have been recently derived, are maintained on mitotically inactivated mouse embryo fibroblasts (MEFs) in 80% KnockOut DMEM (an optimized DMEM for ES cells; GIBCO/BRL), 20% KnockOut SR (a serum-free formulation; GIBCO/BRL), 1 mM glutamine, 0.1 mM 2-mercaptoethanol, 1% nonessential amino acids, 4 ng/ml bFGF, and $10^3$ units/ml LIF which helps maintain the cells in an undifferentiated state. To induce formation of EBs, human ES cells were transferred by using 0.1%/1 mM trypsin/EDTA to plastic Petri dishes to allow their aggregation and prevent adherence to the plate. Human EBs were grown in the same culture medium, except that it lacked LIF and bFGF. The EBs were cultured for 5 days and then dissociated with trypsin and plated on tissue culture plates coated with 50 µg/ml Fibronectin (Boehringer Mannheim). The ES cells were induced to differentiate by growing in the presence of the following human recombinant growth factors: bFGF (10 ng/ml; GIBCO/BRL), transforming growth factor-β1 (TGF-β1; 2 ng/ml; R&D Systems), activin-A (20 ng/ml; R&D Systems), bone morphogenic protein 4 (BMP-4; 10 ng/ml; R&D Systems), hepatocyte growth factor (HGF; 20 ng/ml; R&D Systems), epidermal growth factor (EGF: 100 ng/ml; R&D Systems), β nerve growth factor (NGF; 100 ng/ml; R&D Systems), or retinoic acid (RA; 1 µM; Sigma). The cells were allowed to differentiate for another 10 days under these conditions. These various treatments resulted in the differentiation of the human ES cells into all three embryonic germ layers: mesoderm, endoderm, and ectoderm. Further treatments of the cells with RA and βNGF were capable of increasing the percentage of cells expressing neuronal cell specific markers (Schuldiner, M., Brain Res. (2001) 913:201-205).

One such example of the production of a specific differentiated cell is that of the formation of cardiomyocytes from human ES cells (Kehat, I., J. Clin. Invest. (2001) 108:407-414). Briefly, human ES cells were grown on mitotically inactivated MEF feeder cells in culture medium consisting of 80% KnockOut DMEM, 20% FBS, 1 mM glutamine, 0.1 mM 2-mercaptoethanol, and 1% nonessential amino acids. To induce differentiation, ES cells were dispersed into small clumps using 1 mg/ml collagenase IV (Life Technologies Inc.). The cells were then transferred to plastic Petri dishes where they were cultured in suspension for 7-10 days. The formed EBs were then plated onto 0.1% gelatin-coated culture dishes. The EBs were observed microscopically and approximately 8% of the EBs contained spontaneously contracting areas reminiscent of cardiomyocytes. Significantly, the spontaneously contracting cells expressed a number of cardiac-restricted gene products and transcription factors, displayed electro-physiological properties similar to that of early cardiomyocytes, and exhibited structural features consistent with early-stage cardiac tissue.

Additionally, the recently described ability to genetically manipulate human ES cells should allow for the rapid isolation of highly uniform and singularly differentiated cells (Eiges, R. et al., Current Biol. (2001) 11:514-518). A potential method to this end would be to employ a similar method to that described above for murine ES cells in which antibiotic resistance genes or selectable marker genes are expressed under cell specific promoters. Alternatively, cell-type specific transcription factors or any other cell-type specific factors found to drive cell-type specific differentiation can be expressed. Briefly, the method of genetically manipulating human ES cells entails culturing human ES cells on mitotically inactivated MEF feeder cells in culture medium consisting of 80% KnockOut DMEM, 20% KnockOut SR, 1 mM glutamine, 0.1 mM 2-mercaptoethanol, 1% nonessential amino acids, 50 µg/ml streptomycin, 4 ng/ml bFGF, and $10^3$ units/ml LIF. The cells were then transfected with a plasmid expressing neomycin resistance under the control of an SV40 promoter and green fluorescent protein (GFP) under the control of a promoter that functions in undifferentiated cells. The method of transfection was the chemical transfection reagent ExGen 500 (Fermentas) as human ES cells do not survive electroporation well. Residual transfection reagent is washed away 1 hour later and one day later cells are trypsinized and plated on 100-mm culture dishes containing inactivated $MEF^{Neo+}$ cells. Two days post-replating, G418 (200 ng/ml) was added to the growth medium allowing for selective propagation. At two weeks after selection, over 80% of neomycin resistant cells were found to express GFP. The transfected ES cells were also shown to be capable of forming EBs by removal of bFGF and LIF and allowing aggregation in Perti dishes.

Reproductive Cloning of Non-Human Animals

To date, sheep, cattle, mice and pigs have been cloned successfully. The ability to generate oocytes in accordance with the present invention, facilitates the production of cloned non-human animals which possess genetically superior phenotypic traits.

In an exemplary approach, stem cells are obtained and germ cells derived in accordance with the methods set forth herein. Germ cells so derived are then induced to form either oocytes or spermatogonia. Once oocytes are obtained they may be subjected to the methods set forth in the following patent documents: U.S. Pat. No. 6,258,998 entitled "Methods for cloning porcine animals"; U.S. Pat. No. 6,107,543 "Culture of totipotent embryonic inner cell mass cells and production of bovine animals"; U.S. Pat. No. 6,147,276, "Quiescent cell populations for nuclear transfer in the production of non-human mammals and non-human mammalian embryos" and U.S. Pat. No. 6,215,014 "Cloning using donor nuclei from non-quiescent somatic cells. Given the disclosures of the foregoing patents, the skilled person is readily able to generate non-human animals and embryos using the oocytes provided herein.

Treatment of Infertility Using Oocytes of the Invention

Often infertility is the result of defective oocytes present in the female. In accordance with the methods of the invention, it is now possible to create genetically identical functional oocytes for use in in vitro fertilization methods for the treatment of infertility. In such a method, human stem cells are obtained and germ cells derived as set forth herein. Germ cells so obtained are then differentiated into oocytes. The oocytes are enucleated and a somatic cell nucleus from the infertile female is then transferred into the enucleated oocyte. Blastocysts are then obtained from which stem cells which are genetically identical to the infertile female are isolated. Such stem cells are then treated as described herein to generate a second generation of germ cells. The germ cells are subjected to culture conditions which promote the formation of oocytes which can then be used in in vitro fertilization methods. As mentioned previously, such methods eliminate the moral and ethical concerns and practical difficulties associated with human oocyte harvesting.

It should also be possible to apply the foregoing methods to generate spermatocytes using a male donor somatic cell nucleus for somatic cell nuclear transfer into an enucleated oocyte derived in accordance with the present invention.

The following non-limiting examples are provided to further illustrate the present invention.

Example 1

Generation of GC-Oct4 ES Cells

After feeder cell removal E14 ES cells were resuspended in phosphate-buffered saline (PBS) at a concentration of 1.25× $10^7$ cells/ml. Aliquots (800 µl containing 1×$10^7$ cells) were mixed with 50 µg of the 18 kb NotI fragment of pGC-Oct4 and electroporated with a Bio-Rad Gene Pulser II set at 2.5 kV, 500 μF. Cells were plated onto five 10-cm plates containing a confluent layer of Mitomycin C-treated, neomycin-resistant MEF feeder layers in ES cell medium. After 48 hours and two media changes cells Were fed with ES media containing 350 μg/ml G418 to select for GC-Oct4-positive clones. Two weeks after the start of the selection, resistant clones were identified by Southern analysis using specific primers for eGFP (EGFP-D1: 5'-GCAAGCTGACCCTGAAGTTCATC (SEQ ID NO:2); EGFP-R1: 5'-TCAAGCTGACCCT-GAAGTTCATC (SEQ ID NO:3)).

Example 2

Embryonic Stem Cells

GC-Oct4 ES cells (E14) were grown on Mitomycin C-treated mouse embryonic fibroblast (MEF) cells on 0.1% gelatine-coated tissue culture plates in D-MEM medium containing 4.5 g/l glucose and supplemented with 15% fetal calf serum (Hyclone) and 1 μm β-mercaptoethanol (β-ME) in the presence of 1000 U/ml murine LIF (ESGRO™; Gibco) or in Knockout D-MEM (Gibco) containing 15% Knockout serum replacement (Gibco), 1 μM β-ME and 1000 U/ml murine LIF (ESGRO™; Gibco).

Example 3

Derivation of Early Germ Cells from EBS

ES cell cultures stably transformed with the GC-Oct4 transgene were depleted of MEF cells and cultured as EBs in Knockout D-MEM (Gibco) containing 15% Knockout serum replacement (Gibco) and 1 μM β-ME, using the "hanging drop" method as described by Wobus et al. (Differentiation 1991 48:173-182). Cells (200-600) in 25 μl medium were cultured for 60 hours (with one media change in case of 500 and 600 cells per drop) and then transferred to bacteriological dishes. EBs were maintained floating in the above medium for at least six weeks without significant change in morphology. Medium was changed every week.

Example 4

Direct Differentiation of Germ Cells from EBs into Oocytes

The GC-Oct4 ES cells are depleted of MEF cells and cultured as EBs using a hanging drop method. The EBs are cultured in RPMI 1640 Medium (Hyclone) containing 20% FCS, 1 μM β-ME, 1 mM Na-Pyruvate and penicillin/streptomycin or in ES media without LIF. A small cell number (approximately 300-400) are cultured in a small volume (20 microliters) of medium for about 48 hours and then transferred to tissue culture dishes. About 50 EBs are transferred to a 6-cm tissue culture dish. Outgrowing EBs can be maintained in above medium for at least 16 weeks with the medium being changed every 3 days.

Example 5

Derivation of Early Germ Cells from Adherent ES Cells (for Subsequent Generation of Oocytes)

GC-Oct4 ES cells were grown in tissue culture plates in ES cell medium without MEFs and without LIF at approximately $1$-$2.5 \times 10^4$ cells per $cm^2$. Non-adherent cells were removed and discarded after 3-4 days and medium was replaced. Cultures were maintained in the above medium for additional 3 days before media change and GFP expression was monitored. At that time about 30% of all cells showed GFP expression. Cultures can be carried on for at least 12 weeks when media was changed every 2-3 days.

Cultures can be trypsinized and replated in medium containing 1000 U/ml LIF, 20 ng/ml bFGF (Gibco) and 60 ng/ml murine stem cell factor (SCF; Chemicon Inc) for further cultivation of early germ cells. Alternatively, the trypsinized cultures can be cryo-preserved using standard freezing conditions for ES cells.

This example provides a constant supply of oocytes.

Example 6

Differentiation of Germ Cells Directly Derived from ES Cells into Oocytes

To further improve yield of oocytes, germ cells were first derived as described in example 5 up to the second media change on day 6 or 7. Upon further differentiation a subpopulation of the GFP positive cell population loosens off the plate and forms small aggregates in suspension. These aggregates were collected and transferred to tissue culture plates in ES medium lacking LIF. The transferred cultures were re-fed with fresh medium every 3 days and can be maintained for at least additional 4-6 weeks.

As mentioned previously, the oocytes of the invention may be utilized in a variety of different cloning protocols. However, generating oocytes from ES cells also facilitates methods for screening and characterizing factors and their respective genes which are capable of reprogramming nuclei in a simple system. This system can be genetically modified in a straightforward manner. For example, the expression of cDNA libraries in ES cells should enable the identification of such factors and their respective genes. Once these genes are isolated, it is readily straightforward to manipulate the expression levels of such genes using standard recombinant molecular biology techniques.

In yet another approach, the generation of oocytes from ES cells facilitates screening for and characterization of factors and their respective genes that are involved in germ cell formation. As above, the expression of cDNA libraries in ES cells which contain genes capable of modulating the process of germ cell formation will facilitate the cloning and characterization of such genes.

Finally, it is known that gametes are exquisitely sensitive to many toxic compounds, and their damage has severe consequences for fertility and subsequent normal development. Oocytes generated in accordance with the invention may be utilized in screening methods to determine the toxicity or teratogenic potential of newly developed drugs by assessing follicle growth, oocyte development and embryo formation in vitro.

Methods which enhance follicular growth in vitro, or similar methods, in conjunction with cryopreservation of immature follicles, may also allow the follicle reserves present in the ovaries of a few females to re-establish populations of species currently under the threat of extinction.

In this connection it should be possible to extract immature follicles from valuable livestock for culture in an appropriate system to produce pure-bred embryos to be gestated by genetically unrelated females. The embryos or the follicles could be stored frozen, which would facilitate their preservation and management.

The previous examples and description set forth certain embodiments of the invention. It should be appreciated that not all components or method steps of a complete implementation of a practical system are necessarily illustrated or described in detail. Rather, only those components or method steps necessary for a thorough understanding of the invention have been illustrated and described in detail. Actual implementations may utilize more steps or components or fewer steps or components. Thus, while certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for deriving oocytes from mouse embryonic stem (ES) cells comprising:
   (a) transforming mouse embryonic stem cells with a germ cell specific promoter sequence operably linked to a reporter gene;
   (b) culturing the transformed cells in ES cell medium under conditions which promote differentiation;
   (c) optionally removing the differentiated cells from step b) from said conditions which promote differentiation;
   (d) monitoring the cells of step (b) or (c) for reporter gene expression thereby identifying germ cells in a mixed cell population; and
   (e) isolating oocytes from the germ cells identified from step (d);

wherein said reporter gene encodes a fluorescent protein and wherein said germ cell specific promoter sequence is a truncated Oct4 promoter.

2. The method of claim 1, wherein said oocytes are isolated via a method selected from the group consisting of flow cytometry, enzymatic digestion, and microdissection.

3. The method of claim 1, wherein said differentiation in step b) is promoted by culturing said cells in the absence of leukemia inhibitory factor (LIE).

4. The method of claim 1, wherein said removing of cultured cells from said conditions which promote differentiation in step (c) comprises replating said cultured cells in media comprising LIE, basic fibroblast growth factor (b-EGF) and stem cell factor.

5. The method of claim 1, optionally further comprising subjecting said germ cells identified in step d) to culture conditions which promote the formation of oocyte structures.

6. The method of claim 5, wherein said oocyte structures express zona pellucida protein 3 (ZP3).

7. The method of claim 1, wherein said reporter gene is green fluorescent protein.

8. The method of claim 1, wherein said truncated Oct4 promoter gene sequence is an Oct4 promoter gene sequence with conserved regions 2 and 3 deleted.

9. The method of claim 8, wherein said truncated Oct4 promoter gene sequence is SEQ ID NO: 1.

10. An oocyte obtained by the method of claim 1, wherein said truncated Oct4 promoter gene sequence is an Oct4 promoter gene sequence which lacks conserved regions 2 and 3.

11. An oocyte obtained via the method of claim 5, wherein said truncated Oct4 promoter gene sequence is an Oct4 promoter gene sequence which lacks conserved regions 2 and 3.

12. A method for deriving oocytes from mouse embryonic stem (ES) cells comprising:
   (a) culturing the mouse embryonic stem cells in ES cell medium under conditions which promote differentiation;
   (b) optionally removing the differentiated cells from step a) from said conditions which promote differentiation;
   (c) monitoring the cells of step (a) or (b) for morphological alterations associated with germ cell formation; and
   (d) isolating oocytes from the germ cells identified from the morphological alterations observed in step (c).

13. The method of claim 12, wherein said morphological alterations comprise at least one of the following: cell enlargement, increased spherical appearance, and reduced cell to cell contacts.

14. The method of claim 12, wherein said oocytes are isolated via a method selected from the group consisting of flow cytometry, enzymatic digestion, and microdissection.

15. The method of claim 12, wherein said differentiation in step a) is promoted by culturing said cells in the absence of leukemia inhibitory factor (LIE).

16. The method of claim 12, wherein said removing of cultured cells from said conditions which promote differentiation in step (b) comprises replating said cultured cells in media comprising LIE, basic fibroblast growth factor (b-FGF) and stem cell factor.

17. The method of claim 12, optionally further comprising subjecting said germ cells identified in step c) to culture conditions which promote the formation of oocyte structures.

18. The method of claim 17, wherein said oocyte structures express zona pellucida protein 3 (ZP3).

19. A method for screening test compounds for toxicity or teratogenic potential comprising:
   a) providing an oocyte as claimed in claim 5;
   b) exposing said oocytes to increasing amounts of said test compound; and
   c) culturing said oocytes under conditions that promote blastocyst formation; and
   d) determining the effect, if any, of said test compound on the ability of said oocyte to form a blastocyst.

* * * * *